(12) United States Patent
Guo et al.

(10) Patent No.: US 12,385,923 B2
(45) Date of Patent: Aug. 12, 2025

(54) CLEAVABLE FLUORESCENT TYRAMIDE FOR SENSITIVE AND MULTIPLEXED ANALYSIS OF BIOLOGICAL SAMPLES

(71) Applicant: Arizona Board of Regents on behalf of Arizona State University, Scottsdale, AZ (US)

(72) Inventors: Jia Guo, Tempe, AZ (US); Manas Mondal, Tempe, AZ (US); Renjie Liao, Tempe, AZ (US); Lu Xiao, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 1115 days.

(21) Appl. No.: 17/294,281

(22) PCT Filed: Nov. 11, 2019

(86) PCT No.: PCT/US2019/060768
§ 371 (c)(1),
(2) Date: May 14, 2021

(87) PCT Pub. No.: WO2020/102094
PCT Pub. Date: May 22, 2020

(65) Prior Publication Data
US 2022/0026433 A1   Jan. 27, 2022

Related U.S. Application Data

(60) Provisional application No. 62/767,630, filed on Nov. 15, 2018.

(51) Int. Cl.
G01N 33/00 (2006.01)
G01N 21/64 (2006.01)
G01N 33/58 (2006.01)

(52) U.S. Cl.
CPC .......... *G01N 33/582* (2013.01); *G01N 21/64* (2013.01); *G01N 2021/6439* (2013.01)

(58) Field of Classification Search
CPC .................................................. G01N 33/582
(Continued)

(56) References Cited

U.S. PATENT DOCUMENTS

| 6,066,459 A | 5/2000 | Garini |
| 7,414,116 B2 | 8/2008 | Milton |
| 2017/0254813 A1 | 9/2017 | Bieniarz |

FOREIGN PATENT DOCUMENTS

| JP | 2020504600 A | 2/2020 |
| WO | 2010037395 A2 | 4/2010 |

(Continued)

OTHER PUBLICATIONS

Abdelmohsen, K. et al. RNA-binding protein nucleolin in disease. RNA Biol. 9, 799-808 (2012).

(Continued)

*Primary Examiner* — Elizabeth A Robinson
*Assistant Examiner* — Emily R. Berkeley
(74) *Attorney, Agent, or Firm* — Quarles & Brady, LLP

(57) ABSTRACT

Provided herein are methods for multiplexed in situ analysis of biomolecules in a tissue. In particular, provided herein are methods for multiplexed single-cell in situ protein and nucleic acid profiling in fixed or fresh tissues, and also allows the investigation of the different cell compositions and their spatial organizations in intact tissues through consecutive cycles of probe hybridization, fluorescence imaging, and signal removal.

10 Claims, 27 Drawing Sheets

(58) Field of Classification Search
USPC .......................................................... 436/172
See application file for complete search history.

(56) References Cited

FOREIGN PATENT DOCUMENTS

WO    2016061460 A1    4/2016
WO    2019236841 A1    12/2019

OTHER PUBLICATIONS

Akama, K., et al. Droplet-Free Digital Enzyme-Linked Immunosorbent Assay Based on a Tyramide Signal Amplification System. Anal. Chem. 88, 7123-7129 (2016).
Altelaar, a F. M., et al. Next-generation proteomics: towards an integrative view of proteome dynamics. Nat. Rev. Genet. 14, 35-48 (2012).
Amir, E. D. et al. viSNE enables visualization of high dimensional single-cell data and reveals phenotypic heterogeneity of leukemia. Nat. Biotechnol. 31, 545-52 (2013).
Angelo, M. et al. Multiplexed ion beam imaging of human breast tumors. Nat. Med. 20, 436-442 (2014).
Banerjee, A., et al. PABPN1: molecular function and muscle disease. FEBS J. 280, 4230-50 (2013).
Bayani, J. et al. "Multi-color FISH techniques." Current Protocols in Cell Biology 24.1 (2004): 22-5.
Becskei, A., et al. Contributions of low molecule number and chromosomal positioning to stochastic gene expression. Nat. Genet. 37, 937-944 (2005).
Bendall, S. C. et al. Single-cell mass cytometry of differential immune and drug responses across a human hematopoietic continuum. Science 332, 687-96 (2011).
Blake, W. J., et al. Noise in eukaryotic gene expression. Nature 422, 633-637 (2003).
Blow, N. Tissue preparation: Tissue issues. Nature 448, 959-963 (2007).
Box, J. K. et al. Nucleophosmin: from structure and function to disease development. BMC Mol. Biol. 17, 19 (2016).
Castella, S., et al. Ilf3 and NF90 functions in RNA biology. Wiley Interdiscip. Rev. RNA 6, 243-256 (2015).
Cook, N. P., et al. Detection of a-synuclein amyloidogenic aggregates in vitro and in cells using light-switching dipyridophenazine ruthenium(II) complexes. J. Am. Chem. Soc. 134, 20776-20782 (2012).
Crosetto, N., et al. Spatially resolved transcriptomics and beyond. Nat. Rev. Genet. 16, 57-66 (2014).
Danilova, T. V., et al. "Integrated cytogenetic map of mitotic metaphase chromosome 9 of maize: resolution, sensitivity, and banding paint development." Chromosoma 117.4 (2008): 345-356.
Darmanis, S. et al. A survey of human brain transcriptome diversity at the single cell level. Proc. Natl. Acad. Sci. U. S. A. 112, 7285-90 (2015).
Dore, K., et al. FRET-FLIM investigation of PSD95-NMDA receptor interaction in dendritic spines; control by calpain, CaMKII and Src family kinase. PLoS One 9, (2014).
Duose, D. Y. et al. Configuring robust DNA strand displacement reactions for in situ molecular analyses. Nucleic Acids Res. 40, 3289-98 (2012).
Eisen, M. B., et al. Cluster analysis and display of genome-wide expression patterns. Proc. Natl. Acad. Sci. USA 95, 14863-14868 (1998).
Elowitz, M. B., et al. Stochastic gene expression in a single cell. Science 297, 1183-1186 (2002).
Espina, V. et al. Protein microarrays: Molecular profiling technologies for clinical specimens. Proteomics 3, 2091-2100 (2003).
Fan, R. et al. Integrated barcode chips for rapid, multiplexed analysis of proteins in microliter quantities of blood. Nat. Biotechnol. 26, 1373-8 (2008).
Fransz, P., et al. "Interphase chromosomes in *Arabidopsis* are organized as well defined chromocenters from which euchromatin loops emanate." Proceedings of the National Academy of Sciences 99.22 (2002): 14584-14589.
Gerdes, M. J. et al. Highly multiplexed single-cell analysis of formalin-fixed, paraffin-embedded cancer tissue. Proc. Natl. Acad. Sci. U. S. A. 110, 11982-7 (2013).
Giesen, C. et al. Highly multiplexed imaging of tumor tissues with subcellular resolution by mass cytometry. Nat. Methods 11, 417-422 (2014).
Golding, I., et al. Real-time kinetics of gene activity in individual bacteria. Cell 123, 1025-1036 (2005).
Goltsev, Y. et al. Deep Profiling of Mouse Splenic Architecture with CODEX Multiplexed Imaging. Cell 174, 968-981.e15 (2018).
Guo, J., et al. Multispectral labeling of antibodies with polyfluorophores on a DNA backbone and application in cellular imaging. Proc. Natl. Acad. Sci. U. S. A. 108, 3493-8 (2011).
Gut, G., et al. Multiplexed protein maps link subcellular organization to cellular states. Science (80-.). 361, eaar7042 (2018).
International Searching Authority. International Search Report and Written Opinion for application PCT/US2019/060768. Mailed on Mar. 19, 2020.
Invitrogen. Fish Tag DNA Multicolor Kit instructions (Molecular probes). MP 32951. Oct. 20, 2006. 16 pages.
Jahan, S., et al. Transcription-dependent association of HDAC2 with active chromatin. J. Cell. Physiol. 233, 1650-1657 (2018).
Jean-Philippe, J., et al. hnRNP A1: the Swiss army knife of gene expression. Int. J. Mol. Sci. 14, 18999-9024 (2013).
Jun, Y. W., et al. Addressing the autofluorescence issue in deep tissue imaging by two-photon microscopy: The significance of far-red emitting dyes. Chem. Sci. 8, 7696-7704 (2017).
Kleppe, M. et al. JAK-STAT pathway activation in malignant and nonmalignant cells contributes to MPN pathogenesis and therapeutic response. Cancer Discov. 5, 316-331 (2015).
Klune, J. R., et al. HMGB1: endogenous danger signaling. Mol. Med. 14, 476-84 (2008).
Lake, B. et al. Neuronal subtypes and diversity revealed by single-nucleus RNA sequencing of the human brain. Science (80-.). 357, 352-357 (2015).
Lalmansingh, A. S., et al. TDP-43 is a transcriptional repressor: the testis-specific mouse acrv1 gene is a TDP-43 target in vivo. J. Biol. Chem. 286, 10970-82 (2011).
Lemieux, M. et al. Translocation of CaMKII to dendritic microtubules supports the plasticity of local synapses. J. Cell Biol. 198, 1055-1073 (2012).
Leriche, G., et al. "Cleavable linkers in chemical biology." Bioorganic & medicinal chemistry 20.2 (2012): 571-582.
Liao, R., et al. "Highly sensitive in situ proteomics with cleavable fluorescent tyramide reveals human neuronal heterogeneity." bioRxiv Feb. 8, 2019; doi: https://doi.org/10.1101/539106.
Liao, R.. Highly Multiplexed Single Cell in situ Protein Analysis with Cleavable Fluorescent Probes. Dissertation. Arizona State University, May 2019.
Lin, J.-R., et al. Highly multiplexed imaging of single cells using a high-throughput cyclic immunofluorescence method. Nat. Commun. 6, 8390 (2015).
Lind, D., et al. Characterization of the neuronal marker NeuN as a multiply phosphorylated antigen with discrete subcellular localization. J. Neurosci. Res. 79, 295-302 (2005).
Liu, G., et al. A quantitative evaluation of peroxidase inhibitors for tyramide signal amplification mediated cytochemistry and histochemistry. Histochem. Cell Biol. 126, 283-91 (2006).
Lu, J. et al. Role and molecular mechanism of heterogeneous nuclear ribonucleoprotein K in tumor development and progression. Biomed. reports 4, 657-663 (2016).
Lu, Y. et al. Highly multiplexed profiling of single-cell effector functions reveals deep functional heterogeneity in response to pathogenic ligands. Proc. Natl. Acad. Sci. U. S. A. 607-615 (2015). doi:10.1073/pnas.1416756112.
Martí, A. A., et al. Fluorescent hybridization probes for sensitive and selective DNA and RNA detection. Acc. Chem. Res. 40, 402-409 (2007).

(56) References Cited

OTHER PUBLICATIONS

Mondal, M., et al. Highly Multiplexed Single-Cell Protein Analysis. Chem.—A Eur. J. 1-10 (2018). doi:10.1002/chem.201705014.

Mondal, M., et al. Highly Multiplexed Single-Cell In Situ Protein Analysis with Cleavable Fluorescent Antibodies. Angew. Chemie Int. Ed. 56, 2636-2639 (2017).

Munsky, B., et al. Using Gene Expression Noise to Understand Gene Regulation. Science (80-.). 336, 183-187 (2012).

Ozbudak, E. M., et al. Regulation of noise in the expression of a single gene. Nat. Genet. 31, 69-73 (2002).

Raj, A., et al. Stochastic mRNA synthesis in mammalian cells. PLoS Biol. 4, 1707-1719 (2006).

Raser, J. M. et al. Control of stochasticity in eukaryotic gene expression. Science 304, 1811-1814 (2004).

Roberts, I., et al. "Novel method for the production of multiple colour chromosome paints for use in karyotyping by fluorescence in situ hybridisation." Genes, Chromosomes and Cancer 25.3 (1999): 241-250.

Robertson, D., et al. Multiple immunofluorescence labelling of formalin-fixed paraffin-embedded (FFPE) tissue. BMC Cell Biol. 9, 13 (2008).

Rosenfeld, N., et al. Gene Regulation at the Single-Cell Level. Science 307, 1962-1965 (2005).

Sambrook, et al. eds. Molecular Cloning: A Laboratory Manual, 3rd ed., Cold Spring Harbor Press, Cold Spring Harbor (2001) at Chapter 10.

Schröck, E., et al. "Multicolor spectral karyotyping of human chromosomes." Science 273.5274 (1996): 494-497.

Schubert, W. et al. Analyzing proteome topology and function by automated multidimensional fluorescence microscopy. Nat. Biotechnol. 24, 1270-8 (2006).

Schweller, R. M. et al. Multiplexed in situ immunofluorescence using dynamic DNA complexes. Angew. Chem. Int. Ed. Engl. 51, 9292-6 (2012).

Stack, E. C., et al. Multiplexed immunohistochemistry, imaging, and quantitation: A review, with an assessment of Tyramide signal amplification, multispectral imaging and multiplex analysis. Methods 70, 46-58 (2014).

Van De Corput, M. P., et al. Fluorescence in situ hybridization using horseradish peroxidase-labeled oligodeoxynucleotides and tyramide signal amplification for sensitive DNA and mRNA detection. Histochem. Cell Biol. 110, 431-7 (1998).

Wu, J., et al. Optical imaging techniques in microfluidics and their applications. Lab Chip 12, 3566-3575 (2012).

Xie, R. et al. Factors influencing the degradation of archival formalin-fixed paraffin-embedded tissue sections. J. Histochem. Cytochem. 59, 356-65 (2011).

Xue, M. et al. Chemical methods for the simultaneous quantitation of metabolites and proteins from single cells. J. Am. Chem. Soc. 137, 4066-4069 (2015).

Zhang, W., et al. "Fully automated 5-plex fluorescent immunohistochemistry with tyramide signal amplification and same species antibodies." Laboratory Investigation 97.7 (2017): 873-885.

Zhao, P., et al. Highly Multiplexed Single-Cell Protein Profiling with Large-Scale Convertible DNA-Antibody Barcoded Arrays. Adv. Sci. 1800672, 1800672 (2018).

Zrazhevskiy, P. et al. Quantum dot imaging platform for single-cell molecular profiling. Nat. Commun. 4, 1619 (2013).

FIGS. 11A-11J
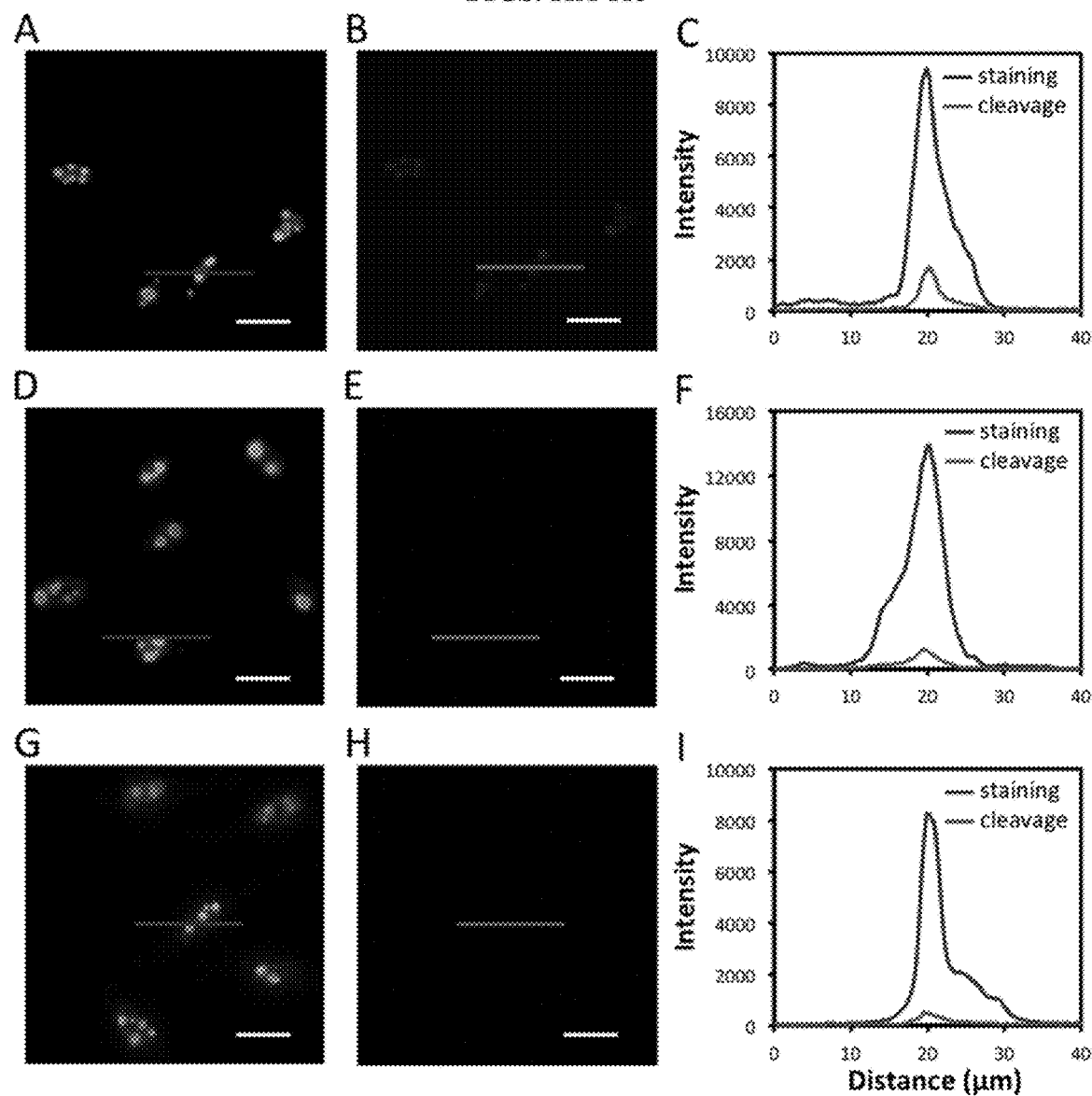
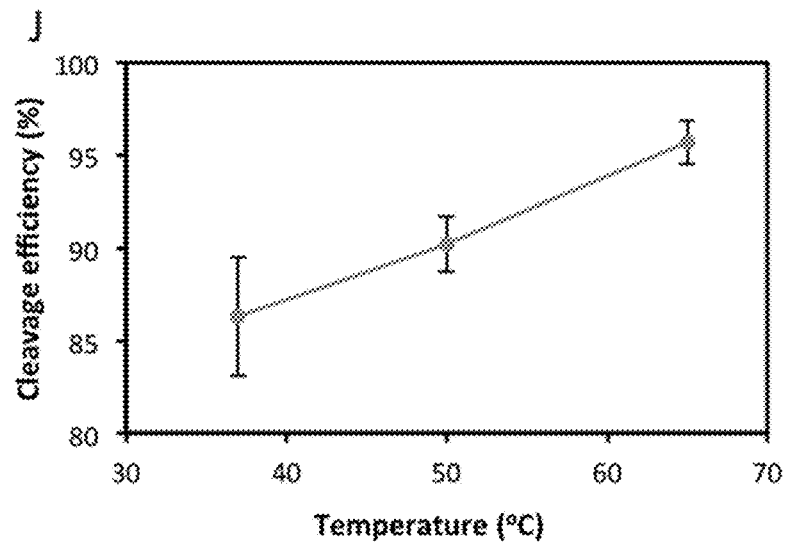

CLEAVABLE FLUORESCENT TYRAMIDE FOR SENSITIVE AND MULTIPLEXED ANALYSIS OF BIOLOGICAL SAMPLES

CROSS-REFERENCE TO RELATED APPLICATIONS

This application is a national stage filing under 35 U.S.C. § 371 of International Application No. PCT/US2019/060768, filed Nov. 11, 2019, which claims the benefit of U.S. Provisional Application No. 62/767,630, filed Nov. 15, 2018, the disclosures of each are hereby incorporated by reference in their entirety for all purposes.

STATEMENT REGARDING FEDERALLY SPONSORED RESEARCH

This invention was made with government support under R01 GM127633 awarded by the National Institutes of Health. The government has certain rights in the invention.

BACKGROUND

The ability to comprehensively profile proteins, nucleic acids, and other biomolecules in intact tissue in situ is crucial to understand the molecular mechanisms underlying cancer, neuroscience, and stem cell biology. The differences between individual cells in complex biological systems may have significant consequences in the function and health of the entire systems. The precise location of multiple, varied biomolecules in a tissue or cell is critical for understanding the spatial organization, gene expression regulation, and interactions of diverse cell types in complex multicellular organisms. However, most of the existing methods for in situ analysis of proteins, nucleic acids, and other biomolecules can only quantify a small number of different molecules in a biological sample. Conventional protein imaging methodologies such as immunohistochemistry (IHC) and immunofluorescence (IF) only allow a handful of proteins to be detected in one tissue sample, and the methods may miss transcripts present at low copy numbers. Accordingly, there remains a need in the art for highly sensitive and multiplexed approaches to in situ protein and nucleic acids analysis.

SUMMARY

The present disclosure overcomes the aforementioned drawbacks by providing low-cost, high-throughput, comprehensive, and highly sensitive and high-quality methods for in situ molecular profiling capable of in situ analysis of target biomolecules (e.g., proteins, nucleic acids) in intact tissues with single-molecule sensitivity.

In a first aspect, provided herein is a method of multiplexed in situ analysis of biomolecules in a tissue. The method can comprise or consist essentially of the following steps: (a) performing a first contacting step that comprises contacting a tissue comprising a plurality of biomolecules to cleavable detectably-labeled tyramide, wherein the first contacting step occurs under conditions that promote conjugation of the cleavable fluorophore-labeled tyramide to a target biomolecule; (b) performing a second contacting step that comprises contacting the tissue with a plurality of horseradish peroxidase (HRP)-conjugated targeting agents that are configured to specifically bind or hybridize to the target biomolecule in the contacted tissue, wherein the second contacting step occurs under conditions that promote binding or hybridization of the targeting agents to the target biomolecule; (c) imaging the cell after the second contacting step whereby a detectable signal generated from an interaction of HRP-conjugated targeting agents with the cleavable fluorophore-labeled tyramide is detected; (d) removing the fluorophore from the fluorophore-labeled tyramide; and (e) optionally, consecutively repeating the contacting, imaging, and removing steps, each time with a new plurality of HRP-conjugate targeting agents for each subsequent cycle, wherein each utilized plurality differs from each other utilized plurality due to being configured to specifically bind or hybridize to a different target biomolecule. The plurality of biomolecules can comprise proteins, RNA, or DNA, or a combination thereof. The cleavable detectably-labeled tyramide can be cleavable fluorescent tyramide (CFT). The detectable label can be a fluorophore. The fluorophore can be selected from the group consisting of Cy5, TAN/IRA, ALEXA FLUOR™ 594, ATTO 647N, and ATTO 700. The HRP-conjugated targeting agents can be HRP-conjugated antibodies or HRP-conjugated oligonucleotides, or a combination thereof. Removing the detectable signal can comprise chemically cleaving the detectable moiety. The method can further comprise washing to remove unhybridized targeting agents and non-specifically hybridized targeting agents following each second contacting step. The plurality of targeting agents can comprise HRP-conjugated synthetic DNA oligonucleotide probes. The plurality of targeting agents can comprise HRP-conjugated polyclonal antibodies, HRP-conjugated monoclonal antibodies, or HRP-conjugated antigen-binding fragments thereof.

In another aspect, provided herein is a kit for detecting target biomolecules in a cell sample. The kit can comprise or consist essentially of a cleavable detectably-labeled tyramide and a written insert component comprising instructions for performing multiplexed in situ analysis of target biomolecules according to methods of this disclosure. The detectable label can be a fluorophore. The fluorophore can be selected from the group consisting of Cy5, TAMRA, ALEXA FLUOR™ 594, ATTO 647N, and ATTO 700. The kit can further comprise a plurality of HRP-conjugated targeting agents configured to bind or hybridize to a target biomolecule. The plurality of HRP-conjugated targeting agents can comprise HRP-conjugated synthetic DNA oligonucleotide probes. The plurality of HRP-conjugated targeting agents can comprise HRP-conjugated polyclonal or monoclonal antibodies, or antigen-binding fragments thereof. The kit can further comprise tris(2-carboxyethyl) phosphine (TCEP) and the written instruction component can further comprise instructions for removing the detectable label from the detectably-labeled tyramide using the TCEP.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or patent application file contains at least one drawing in color. Copies of this patent or patent application publication with color drawings will be provided by the Office upon request and payment of the necessary fee.

FIGS. 11A-11J. (A) Protein Ki67 in HeLa cells is stained with tyramide-$N_3$-Cy5. (B) The stained cells are incubated with TCEP at 37° C. for 30 minutes. (C) Fluorescence intensity profile corresponding to the red and green line positions in (A) and (B). (D) Protein Ki67 in HeLa cells is stained with tyramide-$N_3$-Cy5. (E) The stained cells are incubated with TCEP at 50° C. for 30 minutes. (F) Fluorescence intensity profile corresponding to the red line and green line positions in (D) and (E). (G) Protein Ki67 in HeLa cells is stained with tyramide-$N_3$-Cy5. (H) The stained cells are incubated with TCEP at 65° C. for 30 minutes. (I) Fluorescence intensity profile corresponding to the red line and green line positions in (G) and (H). (J) Fluorophore cleavage efficiency at different reaction temperatures (n=30 positions). Scale bars, 20 μm.

DETAILED DESCRIPTION

The methods and compositions provided herein are based at least in part on the inventors' development of a highly sensitive and multiplexed in situ protein analysis approach that uses a cleavable fluorescent tyramide (CFT) and which has the potential to quantify greater than 50 different proteins in individual cells of intact tissues at the optical resolution. As described herein, this development provides for in situ analysis of proteins, nucleic acids, and other biomolecules in intact tissues with single-molecule sensitivity.

Accordingly, in a first aspect, provided herein is a cleavable detectably-labeled tyramide. In certain embodiments, a detectable label such as a fluorophore is tethered to tyramide via a cleavable linker. Preferably, the cleavable linker is a chemically cleavable linker. As described herein, to enable fluorescence signal removal after protein staining the cleavable detectably labeled tyramide preferably comprises a fluorophore tethered to tyramide through a chemically cleavable linker. An important aspect of the technology of this disclosure is efficient cleavage of the detectable label in a cellular environment while maintaining protein antigenicity. Additionally, it is preferred that the linker is small enough to permit recognition of CFT by horseradish peroxidase (HRP) and to avoid compromised diffusion of a short-lived tyramide radical. In preferred embodiments, the cleavable linker that satisfies these parameters is an azide-based linker or an allyl-based linker. Other cleavable linkers appropriate for use in a CFT of this disclosure include, structures cleaved by enzymes, nucleophiles, electrophiles, reducing reagents, oxidizing reagents, photo-irradiation, metal catalysis, and the like. Further examples of suitable linkers and cleavage mechanisms are described by Milton et al. (U.S. Pat. No. 7,414,116) and by Leriche et al. (*Bioorg. Med. Chem.*, 2012, 20:571-582), which are incorporated herein by reference in their entirety. The linker may be cleavable using a variety of approaches including the addition of a chemical agent, irradiation with one or more wavelengths of light, enzymatic reaction and the like.

In one embodiment, a cleavable fluorescent tyramide is tyramide-N$_3$-Cy5, having the following chemical structure (II):

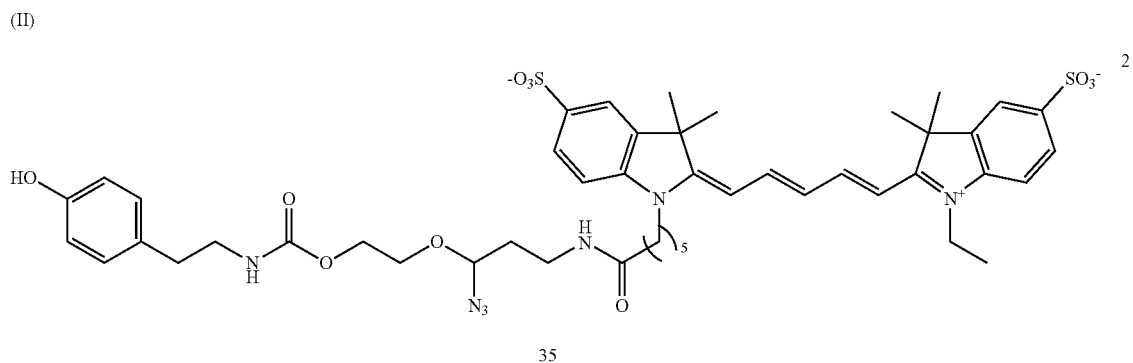

Figure 23:
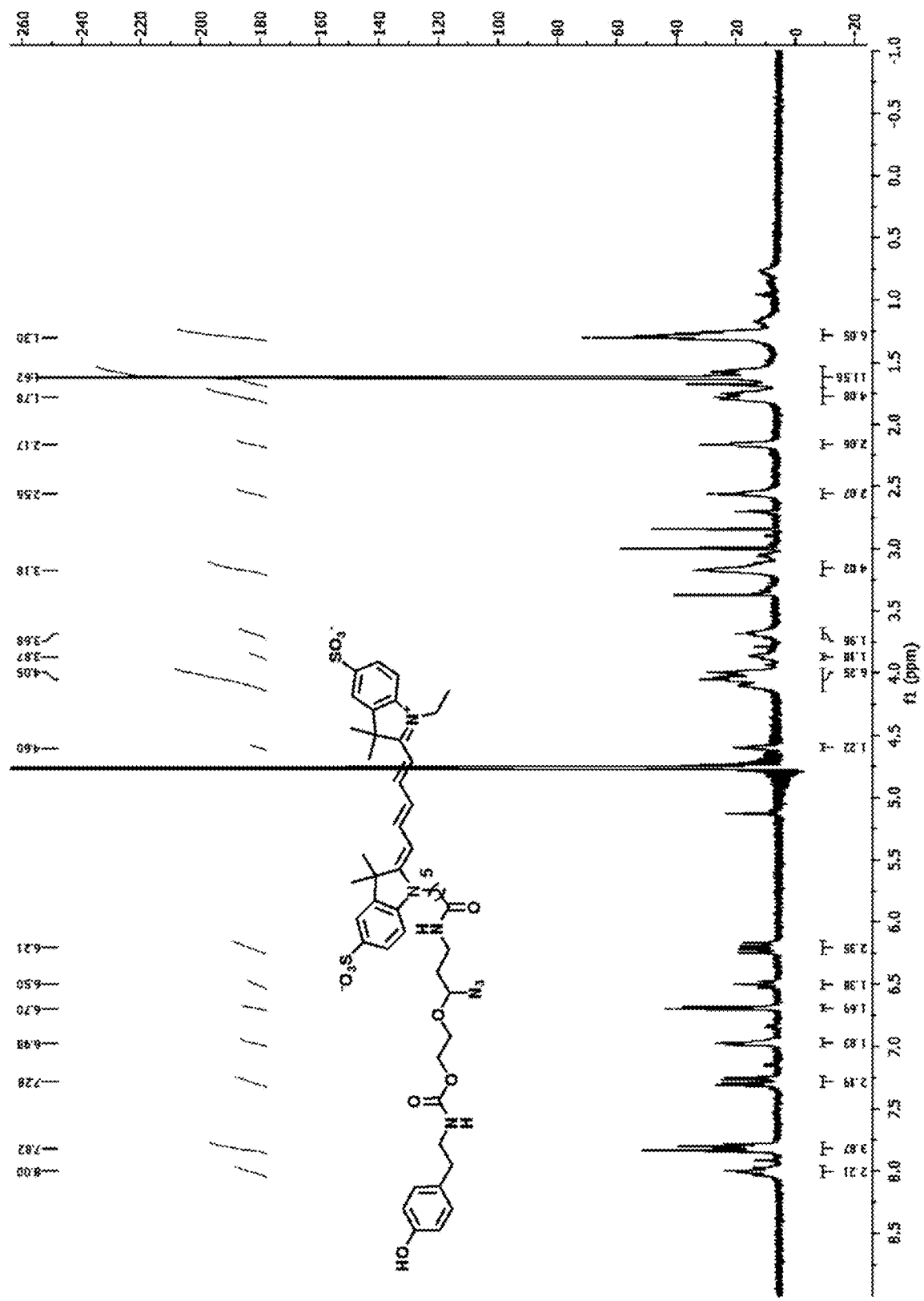
FIG. 23. $^1$H NMR of tyramide-N$_3$-Cy5 (500 MHz, CD3OD).

Tyramide-N$_3$-Cy5 was designed and synthesized (FIG. 1B) by tethering fluorophore Cy5 to tyramide through an azide-based cleavable linker. The synthesis and characterization of tyramide-N$_3$-Cy5 is described in Example 2. NMR for tyramide-N$_3$-Cy5 is shown in FIG. 23.

Any appropriate detectable label can be used to produce a cleavable detectably-labeled tyramide. In some cases, the detectable label of the cleavable detectably-labeled tyramide is a fluorophore. In such cases, the cleavable detectably-labeled tyramide is cleavable fluorescent tyramide (CFT). Appropriate fluorophores for use in the methods of this disclosure include, without limitation, Cy5, TAMRA (labeled with tetramethylrhodamine or "TMR"), ALEXA FLUOR™ 594 ((13-[2-carboxy-(4 or 5)-(2,5-dioxopyrrolidin-1-yl)oxycarbonylphenyl]-6,7,7,19,19,20-hexamethyl-17-(sulfomethyl)-2-oxa-20-aza-6-azoniapentacyclo [12.8.0.0$^{3,12}$.0$^{5,10}$.0$^{16,21}$]docosa-1 (14),3,5,8,10.12.15,17, 21-nonaen-9-yl) methanesulfonate), and ATTO 647N and ATTO 700 fluorophores (ATTO-TEC, Germany). Other fluorophores appropriate for use according to the methods provided herein include, without limitation, quantum dots, ALEXA FLUOR™ 350, ALEXA FLUOR™ 532, ALEXA FLUOR™ 546, ALEXA FLUOR™ 568, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, DYLIGHT™ DYES (e.g., DYLIGHT™ 405, DYLIGHT™ 488, DYLIGHT™ 549, DYLIGHT™ 594, DYLIGHT™ 633, DYLIGHT™ 649, DYLIGHT™ 680, DYLIGHT™ 750, DYLIGHT™ 800 and the like), Texas Red, and Cy2, Cy3.5, Cy5.5, and Cy7. In addition to the use of fluorophores as a detectable moiety, other labels such as luminescent agents (e.g., chemiluminescent agents), quantum dots, fluorescent proteins, and radioisotopes can also be used as detection tags.

Figures 1A, 1B:
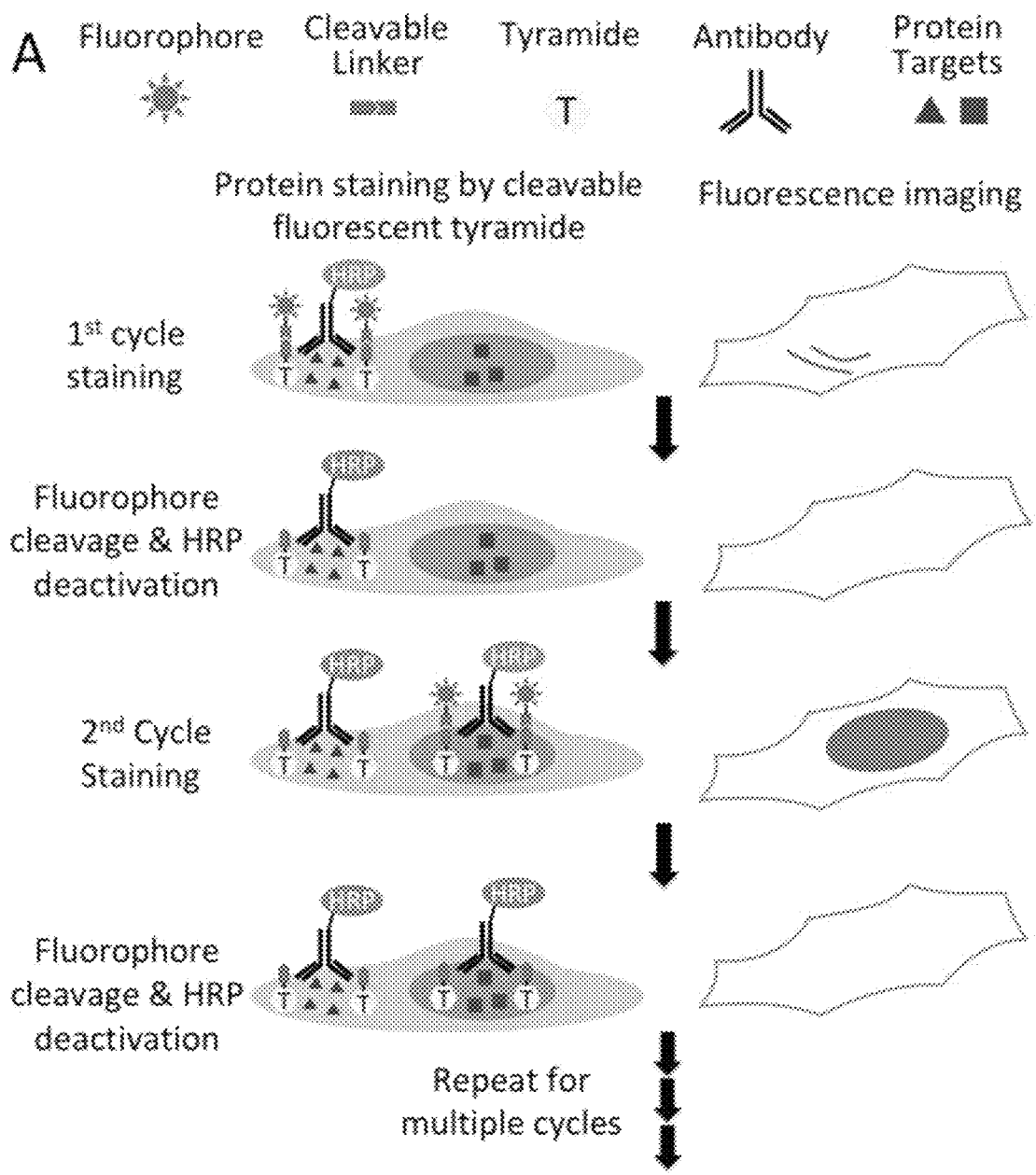
FIGS. 1A-1B. (A) Highly sensitive and multiplexed in situ protein profiling with cleavable fluorescent tyramide. Protein targets are stained with HRP conjugated antibodies and cleavable fluorescent tyramide. After imaging, the fluorophores are chemically cleaved and simultaneously the HRP is deactivated. Through cycles of target staining, fluorescence imaging, fluorophore cleavage, and HRP deactivation, comprehensive protein profiling can be achieved in single cells in situ. (B) Structure of cleavable fluorescent tyramide, tyramide-$N_3$-Cy5.

In another aspect, provided herein is a method for multiplexed in situ analysis of biomolecules in a tissue. As used herein, the term "multiplexed" refers to the detection of multiple signals (e.g., two or more signals), such as, for example, analytes, fluorescent signals, analog or digital signals, that are combined into one signal over a shared medium. The term encompasses the detection of multiple signals simultaneously in a single sample or single reaction vessel, as well as the combining of images of multiple signals to obtain one image that reflects the combination. Referring to FIG. 1A, the method comprises three steps in each analysis cycle. First, for analysis of a protein in a tissue, the tissue is contacted with a horseradish peroxidase (HRP)-conjugated antibody configured to bind specifically to the protein target. For analysis of nucleic acids in a tissue, the tissue is contacted with a HRP-conjugated oligonucleotide probe configured to hybridize to the nucleic acid target. The tissue is also contacted with a detectably-labeled, cleavable tyramide. HRP catalyzes the coupling reaction between the cleavable tyramide and tyrosine residues on an endogenous protein target in close proximity. In the second step, fluorescence images are captured to generate quantitative protein expression profiles. Finally, detectable labels attached to the cleavable tyramide are chemically cleaved in step that simultaneously deactivates HRP, which allows for initiation of the next analysis cycle. Through reiterative cycles of target staining, fluorescence imaging, fluorophore cleavage, and HRP deactivation, a large number of different target biomolecules with a wide range of expression levels can be quantified in single cells of intact tissues in situ.

In exemplary embodiments, the method comprises (a) performing a first contacting step that comprises contacting a tissue comprising a plurality of biomolecules to cleavable detectably-labeled tyramide, wherein the first contacting step occurs under conditions that promote conjugation of the cleavable detectably labeled tyramide to a target biomolecule; (b) performing a second contacting step that comprises contacting the tissue with a plurality of horseradish peroxidase (HRP)-conjugated targeting agents that are configured to specifically bind or hybridize to the target biomolecule in the contacted tissue, where the second contacting step occurs under conditions that promote binding or hybridization of the targeting agents to the target biomolecule; (c) imaging the cell after the second contacting step whereby a detectable signal generated from an interaction of HRP-conjugated targeting agents with the cleavable detectably labeled tyramide is detected; (d) removing the detectable label from the detectably labeled tyramide; and (e) optionally consecutively repeating the contacting, imaging, and removing steps, each time with a new plurality of HRP-conjugate targeting agents for each subsequent cycle, where each utilized plurality differs from each other utilized plurality due to being configured to specifically bind or hybridize to a different target biomolecule.

The targeting agent will vary depending on the type of target biomolecule. In some cases, the target biomolecule is a protein or peptide. In such cases, the targeting agent will be an antibody that specifically binds to the target protein or peptide. For example, if the target biomolecule is protein Histone deacetylase 2 (HDAC2), the target agents comprise anti-HDAC2 antibodies conjugated to HRP. Antibodies suitable for the methods include, without limitation, polyclonal antibodies, monoclonal antibodies, and antigen-binding fragments thereof. HRP-conjugated antibodies can be used to detect other target biomolecules such as lipids and metabolites.

In other cases, the target biomolecule is a nucleic acid (e.g., DNA, RNA). In such cases, the targeting agent will be a HRP-conjugated oligonucleotide having sequence complementary to the target nucleic acid sequence. Under appropriate conditions, the HRP-oligonucleotide will hybridize to the target nucleic acid sequence. In some cases, multiple cycles of the method are performed to detect multiple target biomolecules using targeting agents that are HRP-conjugated antibodies, HRP-conjugated oligonucleotides, or a combination thereof.

In some cases, the target biomolecule is a carbohydrate. In such cases, the targeting agent can be a HRP-conjugated lectin that is capable of binding carbohydrate. As used herein, the term "lectin" refers to a protein or glycoprotein that binds to specific carbohydrate structures to form a lectin-carbohydrate complex. The term encompasses lectins derived from animal and plant sources, and which bind carbohydrates by affinity. The term "lectin" as used herein also encompasses glycoproteins and proteins not normally termed lectins but which immunologically bind carbohydrates, such as antibodies, e.g., monoclonal antibodies. Since lectins bind selectively to some but not all carbohydrates (e.g., monosaccharides, such as mannose, GleNAc, gelatose, a-fructose or sialic acid) to different degrees, it will be understood that the type of lectin conjugated to HRP will vary depending on the target carbohydrate of interest.

Any appropriate method of preparing antibody-horseradish peroxidase conjugates can be used. Exemplary protocols for preparation of an HRP antibody conjugate are known in the art. By way of non-limiting example, HRP can be activated for conjugation by treatment with a 100-fold molar excess of a bifunctional PEG linker having a maleimide group and an active ester group. Antibodies to a protein of interest can be prepared for conjugation by introducing thiols using, for example, DTT. A thiolated antibody can be contacted to a molar excess of HRP comprising a bifunctional PEG linker for conjugation.

In some cases, the HRP-conjugated detection agent (e.g., antibody, oligonucleotide) and cleavable detectably labeled tyramide are contacted in the presence of a tyramide signal amplification buffer. In some cases, the amplification buffer comprises an aqueous phosphate-buffered, borate-buffered, or other buffered solution to which low concentrations of hydrogen peroxide are added. In some cases, the amplification buffer comprises 0.0015% $H_2O_2$ and 0.1% TRITON™ X-100 (2-[4-(2,4,4-trimethylpentan-2-yl) phenoxy]ethanol) in 0.1 M boric acid, pH=8.5. Commercial tyramide signal amplification buffers are available from several manufacturers including, for example, PerkinElmer, ThermoFisher, and Biotium.

In some cases, the "removing" step comprises chemically cleaving the detectable label. Any appropriate means of removing a detectable signal or detectable label (e.g., a fluorophore) can be used according to the methods provided herein. Methods of removal can include without limitation photobleaching, chemical deactivation, chemical cleavage of the fluorophores (see the Examples below), enzymatic cleavage of the fluorophores, DNA/RNA strand displacement, chemical or heat denaturing of an intermediate fluorescent oligonucleotide, and the like. Since photobleaching can be a time-consuming step, in some cases the methods provided herein comprise efficiently removing fluorescence signals by chemical deactivation or chemical or enzymatic cleavage of detectable labels.

In some cases, the methods provided herein comprise chemical inactivation of fluorophores. For example, fluorophores can be inactivated by oxidation. Protocols for oxidation of dyes with hydrogen peroxide, which can be catalyzed using either acidic or basic conditions, or reactive oxygen species (ROS) are known to those practitioners in the art for changing the fluorescent properties of dyes and fluorescent proteins.

When fluorescently labeled tyramide is used, fluorescence photomicroscopy can be used to detect and record the results of consecutive in situ analysis using routine methods known in the art. Alternatively, digital (computer implemented) fluorescence microscopy with image-processing capability may be used. Two well-known systems for imaging FISH of chromosomes having multiple colored labels bound thereto include multiplex-FISH (M-FISH) and spectral karyotyping (SKY). See Schrock et al. (1996) *Science* 273:494; Roberts et al. (1999) *Genes Chrom. Cancer* 25:241; Fransz et al. (2002) *Proc. Natl. Acad. Sci. USA* 99:14584; Bayani et al. (2004) *Curr. Protocol. Cell Biol.* 22.5.1-22.5.25; Danilova et al. (2008) *Chromosoma* 117:345; U.S. Pat. No. 6,066,459; and FISH TAG™ DNA Multicolor Kit instructions (Molecular probes) for a review of methods for painting chromosomes and detecting painted chromosomes.

To minimize issues of autofluorescence or background signal, oligonucleotide targeting agents can be designed to hybridize to a target nucleic acid at multiple places on the target nucleic acid sequence. Thus, an increased number of oligonucleotides will hybridize to each target nucleic acid sequence (e.g., transcript) to enhance signal to noise ratio. As used herein, the terms "binding," "to bind," "binds," "bound," or any derivation thereof refers to any stable, rather than transient, chemical bond between two or more molecules, including, but not limited to, covalent bonding, ionic bonding, and hydrogen bonding. The term "binding" encompasses interactions between polypeptides, for example, an antibody and its epitope on a target protein. The term also encompasses interactions between a nucleic acid molecule and another entity such as a nucleic acid or probe element. Specifically, binding, in certain embodiments, includes the hybridization of nucleic acids. In some cases, the methods further comprise a blocking step to reduce background signal. The term "blocking" as used herein refers to treatment of a sample with a composition that prevents the non-specific binding of the target substance to the sample. Typically a blocking composition comprises a protein, such as casein or albumin, and may additionally comprise surfactants. The function of the protein is to bind to the sample to prevent the non-specific binding of assay reagents.

In some cases, the method further comprises a washing step. For example, the method can further comprise washing to remove unhybridized targeting agents and non-specifically hybridized targeting agents following the second contacting step.

The methods of this disclosure can be performed using a tissue sample obtained from any biological entity. The term "biological entity" as used herein means any independent organism or thing, alive or dead, containing genetic material (e.g., nucleic acid) that is capable of replicating either alone or with the assistance of another organism or cell. Sources for nucleic acid-containing biological entities include, without limitation, an organism or organisms including a cell or cells, bacteria, yeast, fungi, algae, viruses, or a sample thereof. Specifically, an organism of the current disclosure includes bacteria, algae, viruses, fungi, and mammals (e.g., humans, non-human mammals). The methods and compositions described herein can be performed using a variety of biological or clinical samples comprising cells that are in any (or all) stage(s) of the cell cycle (e.g., mitosis, meiosis, interphase, G0, G1, S and/or G2). As used herein, the term "sample" include all types of cell culture, animal or plant tissue, peripheral blood lymphocytes, buccal smears, touch preparations prepared from uncultured primary tumors, cancer cells, bone marrow, cells obtained from biopsy or cells in bodily fluids (e.g., blood, urine, sputum and the like), cells from amniotic fluid, cells from maternal blood (e.g., fetal cells), cells from testis and ovary, and the like. In some cases, samples are obtained by swabbing, washing, or otherwise collecting biological material from a non-biological object such as a medical device, medical instrument, handrail, door knob, etc. Samples are prepared for assays of this disclosure using conventional techniques, which typically depend on the source from which a sample or specimen is taken. These examples are not to be construed as limiting the sample types applicable to the methods and/or compositions described herein.

In some cases, the methods provided herein comprise a cell or tissue fixation step. For example, the cells of a biological sample (e.g., tissue sample) can be fixed (e.g., using formalin, formaldehyde, or paraformaldehyde fixation techniques known to one of ordinary skill in the art). In some cases, the tissue is formalin-fixed and paraffin-embedded (FFPE). Any fixative that does not affect antibody binding or nucleic acid hybridization can be utilized in according to the methods provided herein. In other cases, the methods are performed on unfixed ("fresh") tissue samples.

As described herein, the methods of the present invention provide for multiplexed in situ analysis of biomolecules in a tissue. Through consecutive cycles of targeting agent binding/hybridization, fluorescence imaging, and signal removal, different biomolecule species can be identified as fluorescent spots with unique color sequences.

As used herein, the term "biomolecule" or "biological molecule" refers to any molecule that is substantially of biological origin and encompasses proteins, peptides, and nucleic acids. Such molecules may include non-naturally occurring components that mimic a naturally occurring component, e.g., a non-naturally occurring amino acid. The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer. As used herein, the terms "nucleic acid" or "oligonucleotide" refer to and encompass any physical string or collection of monomer units (e.g., nucleotides) that can connect to form a string of nucleotides, including a polymer of nucleotides (e.g., a typical DNA or RNA polymer), peptide nucleic acids (PNAs), modified oligonucleotides (e.g., oligonucleotides comprising nucleotides that are not typical to biological RNA or DNA, such as 2'-O-methylated oligonucleotides), and the like. The nucleotides of the nucleic acid can be deoxyribonucleotides, ribonucleotides or nucleotide analogs, and can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. The nucleic acid can additionally comprise non-nucleotide elements such as labels, quenchers, blocking groups, or the like. The nucleic acid can be single-stranded or double-stranded.

As used herein, the terms "nucleic acid of interest," and "target nucleic acid" include a nucleic acid originating from one or more biological entities within a sample. The target nucleic acid of interest to be detected in a sample can be a sequence or a subsequence from DNA, such as nuclear or mitochondrial DNA, or cDNA that is reverse transcribed from RNA in the sample. The sequence of interest can also be from RNA, such as mRNA, rRNA, tRNA, miRNA, siRNAs, antisense RNAs, or long noncoding RNAs. More generally, the sequences of interest can be selected from any combination of sequences or subsequences in the genome or transcriptome of a species or an environment. In some cases, a defined set of targeting agents are oligonucleotide probes that are designed to hybridize to the plurality of sequences that would be expected in a sample, for example a genome or transcriptome, or a smaller set when the sequences are known and well-characterized, such as from an artificial source.

Oligonucleotide probes useful for the methods provided herein are of any length sufficient to permit probe penetration and to optimize hybridization of probes for in situ analysis according to the methods of this disclosure. Preferably, probe length is about 20 bases to about 500 bases. As probe length increases, so increases the number of binding sites that can be incorporated into a given probe for hybridization to the probe of the following cycle as well as the signal to noise ratio. However, longer than 500 bases, the probes may not efficiently penetrate the cellular membrane. Preferably, the oligonucleotide probes have a probe length between 20 and 500 nucleotides, 20 and 250, 50 and 250, 150 and 250 nucleotides, 20 and 150, or 50 and 150 nucleotides, inclusive.

The terms "hybridize" and "hybridization" as used herein refer to the association of two nucleic acids to form a stable duplex. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, N.Y.). One of skill in the art will understand that "hybridization" as used herein does not require a precise base-for-base complementarity. That is, a duplex can form, between two nucleic acids that contained mismatched base pairs. The conditions under which nucleic acids that are perfectly complementary or that contain mismatched base pairs will hybridize to form a duplex are well known in the art and are described, for example, in MOLECULAR CLONING: A LABORATORY MANUAL, $3^{rd}$ ed., Sambrook et al., eds., Cold Spring Harbor Press, Cold Spring Harbor (2001) at Chapter 10, which is herein incorporated by reference. As used herein, the term "complementary" refers to a nucleic acid that forms a stable duplex with its "complement". For example, nucleotide sequences that are complementary to each other have mismatches at less than 20% of the bases, at less than about 10% of the bases, preferably at less than about 5% of the bases, and more preferably have no mismatches.

Kits

In another aspect, provided herein is a kit comprising reagents for performing multiplexed in situ analysis of biomolecules in a tissue. Preferably, the kit comprises a cleavable detectably-labeled tyramide and a written insert component comprising instructions for performing multiplexed in situ analysis of target biomolecules according to the methods provided herein. In some cases, the detectable label is a fluorophore (e.g., Cy5, TAMRA, ALEXA FLUOR™ 594, ATTO 647N, ATTO 700). In some cases, the kit further comprises a one or more HRP-conjugated targeting agents configured to bind or hybridize to a target biomolecule. As described herein, the targeting agents can be synthetic DNA oligonucleotide probes, polyclonal antibodies, monoclonal antibodies, antigen-binding fragments of an antibody, or some combination thereof. In some cases, the plurality of HRP-conjugated targeting agents comprises HRP-conjugated synthetic DNA oligonucleotide probes. In some cases, the plurality of HRP-conjugated targeting agents comprises HRP-conjugated polyclonal or monoclonal antibodies, or antigen-binding fragments thereof. In some cases, the kit further comprises an amplification reaction buffer, a blocking reagent, and/or a hydrogen peroxide additive.

A kit will preferably include instructions for employing the kit components as well the use of any other reagent not included in the kit. Instructions may include variations that can be implemented. In some cases, the kit further comprises tris(2-carboxyethyl)phosphine (TCEP) or another agent for removing the detectable label from tyramide. In such cases, the written instruction component further comprises instructions for removing the detectable label from the detectably-labeled tyramide using the TCEP or other removing agent.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As used herein and in the appended claims, the singular forms "a", "an" and "the" include plural reference, unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. In addition, the terms "comprising", "including" and "having" can be used interchangeably.

As used herein, "about" means within 5% of a stated concentration range or within 5% of a stated time frame.

Various embodiments and aspects of the present invention as delineated hereinabove and as claimed in the claims section below find experimental support in the following examples which, together with the above descriptions, illustrate some embodiments of the invention in a non-limiting fashion.

EXAMPLES

Example 1: Highly Sensitive and Multiplexed in Situ Protein Profiling with Cleavable Fluorescent Tyramide Reveals Human Neuronal Heterogeneity This example demonstrates a highly sensitive and multiplexed in situ protein analysis approach using a cleavable fluorescent tyramide (CFT). Through reiterative cycles of target staining, fluorescence imaging, fluorophore cleavage and horseradish peroxidase deactivation, this approach has the potential to sensitively detect hundreds of proteins in intact tissues at the optical resolution. As demonstrated in this section, horseradish peroxidase (HRP) conjugated antibodies were applied to recognize their target proteins and catalyze the enzymatic deposition of CFT. After fluorescence imaging, the deposited fluorophores were efficiently cleaved, while HRP was deactivated simultaneously. Through reiterative staining cycles, this approach has the potential to sensitively detect greater than 50 different proteins in the same tissue at the optical resolution. Applying this approach, we studied protein expression heterogeneity in a population of genetically identical cells, and performed protein expression correlation analysis to identify co-regulated proteins. We also profiled >6000 neurons in a human formalin-fixed paraffin-embedded (FFPE) hippocampus tissue. By partitioning these neurons into varied cell clusters based on their multiplexed protein expression profiles, we observed different subregions of the hippocampus consist of neurons from distinct clusters. This comprehensive in situ protein profiling technology will bring new insights into systems biology, molecular diagnosis and cellular targeted therapies.

To enable fluorescence signal removal after protein staining, we designed CFT by tethering fluorophores to tyramide through a chemically cleavable linker. A critical requirement for the success of this technology is to efficiently cleave the fluorophores in the cellular environment while maintaining the protein antigenicity. Additionally, it is preferred that the linker has a small size, so that HRP can still recognize CFT as a good substrate and the diffusion of short-lived tyramide radical is not compromised. Recently, our laboratory has developed an azide-based cleavable linker, which satisfies all of those requirements. Thus, we incorporated that linker into CFT. Most tissues exhibit prominent autofluorescence from the green and yellow emission channels, while only minimal autofluorescence is detected in the red emission channel. To avoid the significant green and yellow autofluorescence background, in the current study we selected Cy5 as the fluorophore for CFT. CFT (tyramide-$N_3$-Cy5) was designed and synthesized (FIG. 1B) by tethering Cy5 to tyramide through an azide-based cleavable linker. The synthesis and characterization of CFT is described in Example 2. NMR for CFT is shown in FIG. 23.

Figures 2A, 2B, 2C, 2D:
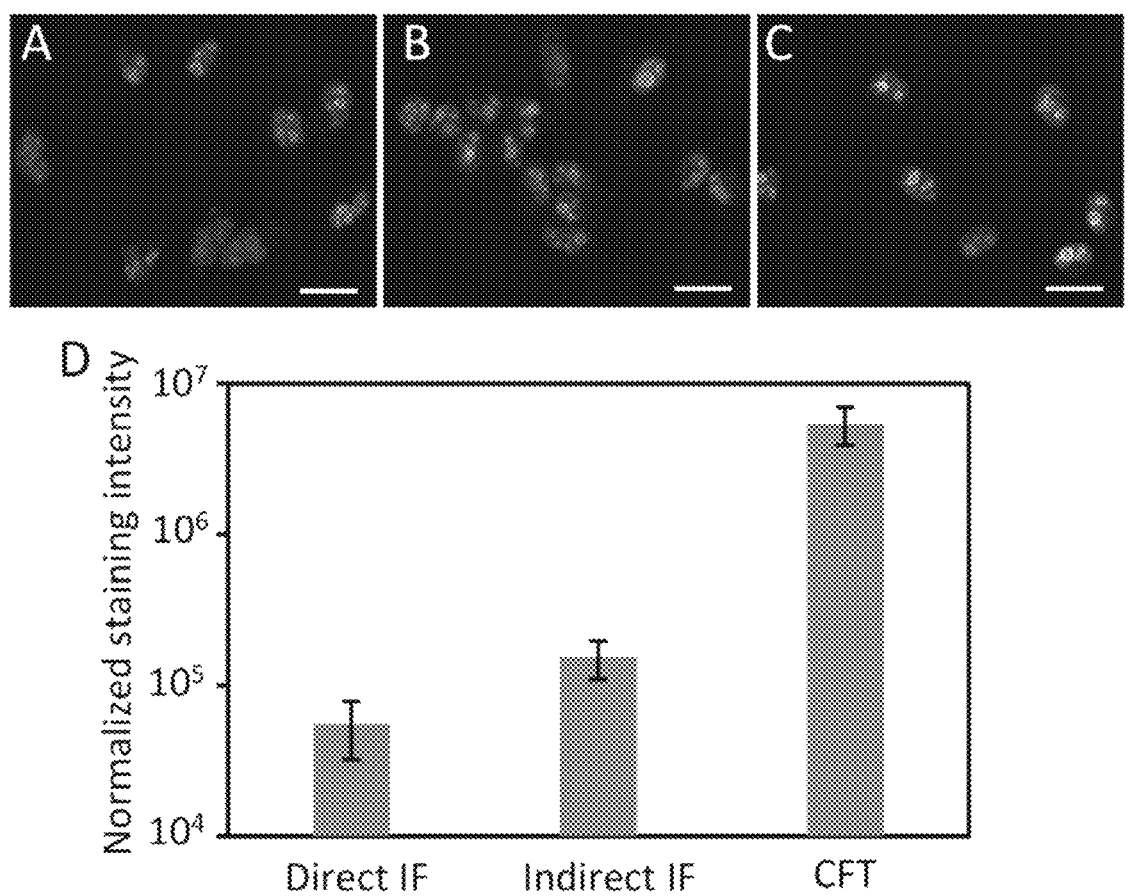
FIGS. 2A-2D. Expression of protein Ki67 is shown in in HeLa cells stained by (A) direct immunofluorescence (IF), (B) indirect IF, and (C) cleavable fluorescent tyramide (CFT). The images in (A), (B) and (C) are captured with the exposure time of 1 second, 300 millisecond, and 15 millisecond, respectively. (D) Normalized staining intensities of 30 different positions in (A), (B) and (C). The y-axis in (D) is on a logarithmic scale. Scale bars, 25 μm.
Figures 3A, 3B, 3C, 3D:
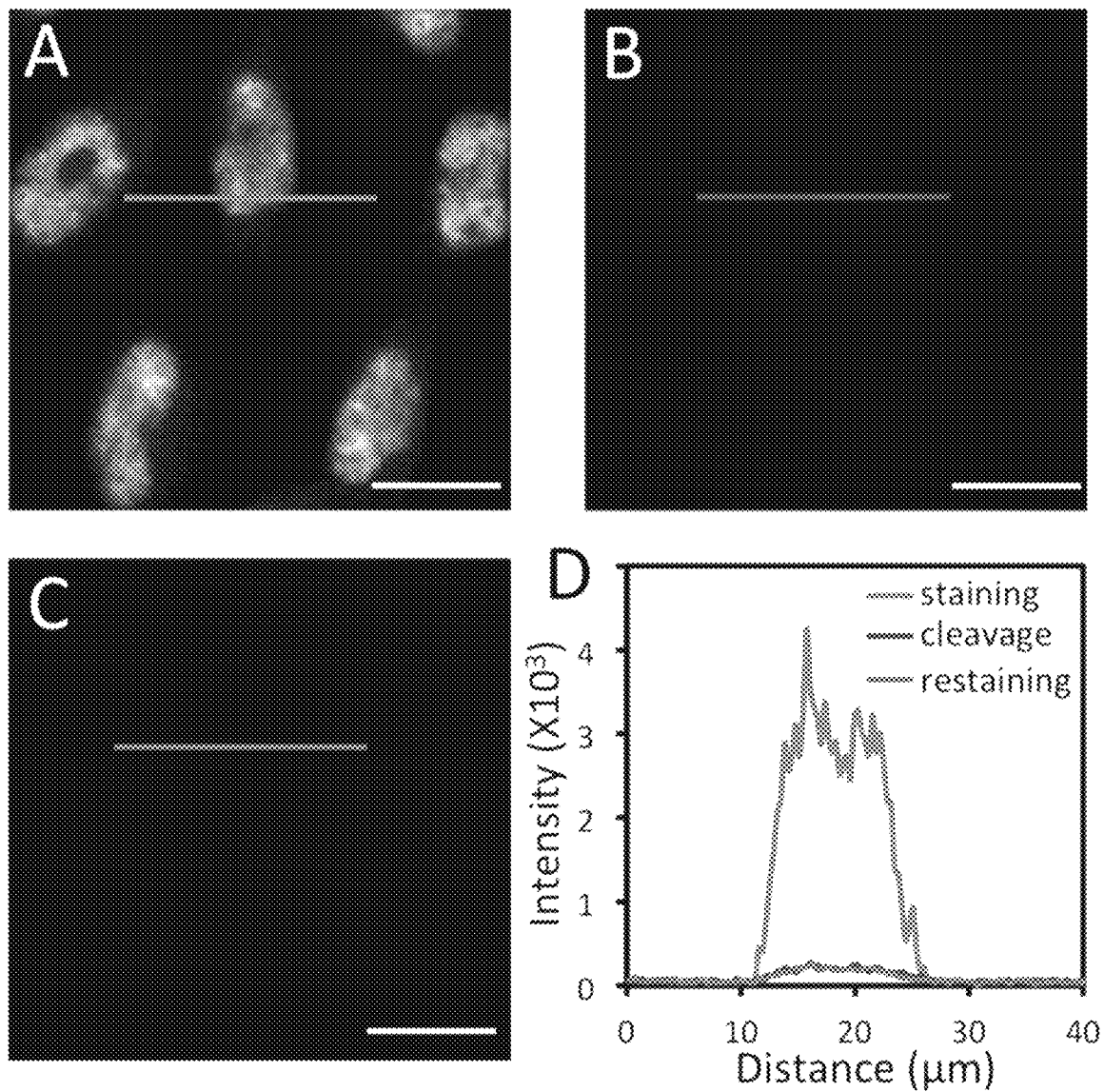
FIGS. 3A-3D. (A) Expression of protein ILF3 in HeLa cells is stained with HRP conjugated antibodies and tyramide-$N_3$-Cy5. (B) Cy5 is cleaved by TCEP. (C) Cells are incubated with tyramide-$N_3$-Cy5, again. (D) Fluorescence intensity profile corresponding to the red, blue and green line positions in (A), (B) and (C). Scale bars, 20 μm.

Detection sensitivity of the protein analysis approach was assessed by comparing it with direct and indirect immunofluorescence, which have similar sensitivity to the current multiplexed in situ protein profiling approaches. Applying conventional immunofluorescence methods, we stained protein Ki67 in HeLa cells with Cy5 labeled primary antibodies (FIG. 2A), and unlabeled primary antibodies together with Cy5 labeled secondary antibodies (FIG. 2B). Using our approach, protein Ki67 was stained with unlabeled primary antibodies and HRP conjugated secondary antibodies along with tyramide-$N_3$-Cy5 (FIG. 2C). With primary antibodies of the same concentration, our method is ~88 and ~35 times more sensitive than direct and indirect immunofluorescence, respectively (FIG. 2D). Additionally, the staining resolution of the three methods closely resembles each other (FIGS. 2A-2C). These results suggest that HRP can still recognize CFT as a good substrate and the incorporation of the cleavable linker into CFT does not interfere with the diffusion of the CFT radical. More importantly, the extremely high sensitivity of our approach enables the quantitative in situ analysis of low-abundance proteins, which could be undetectable by the reported methods. Moreover, by reducing the imaging time by 1-2 orders of magnitude, our method allows a large number of individual cells to be profiled in a short time, which leads to the dramatically improved sample throughput and minimized assay time.

Efficient Fluorophore Cleavage Without Loss of Protein Antigenicity

The inventors next explored whether the fluorophores can be efficiently cleaved while maintaining the protein antigenicity. To search for this ideal cleavage condition, we stained protein Ki67 in HeLa cells using HRP conjugated antibodies and tyramide-$N_3$-Cy5, and evaluated the fluorophore cleavage efficiencies at different temperature. After incubating with tris(2-carboxyethyl)phosphine (TCEP) at 37° C., 50° C. and 65° C. for 30 minutes, over 85%, 90% and 95% of the staining signals were removed, respectively (FIGS. 11A-11J).

To test whether the protein antigenicity remains at those varied cleavage temperature, the inventors incubated HeLa cells with TCEP at 37° C., 50° C. and 65° C. for 24 hours, and subsequently stained protein Ki67 with tyramide-$N_3$-Cy5. The inventors also labeled protein Ki67 without any pre-treatment as controls. The cells with the TCEP incubation at 37° C. and 50° C. had similar staining intensities to the control cells; while the cells pretreated at 65° C. only had about half of the staining intensities compared to the control cells (FIGS. 12A-12E). We then studied the fluorophore cleavage kinetics at 50° C. by incubating the stained cells with TCEP for 5, 15, 30 and 60 minutes. Among these conditions, 30 minutes was identified as the minimum cleavage time required to achieve the maximum cleavage efficiency (FIGS. 13A-13M). These results suggest that the TCEP treatment at 50° C. for 30 minutes is the ideal condition to efficiently remove the fluorescence signals generated by protein staining with CFT, and this condition preserves the protein antigenicity.

Simultaneous Fluorophore Cleavage and HRP Activation

Another critical requirement for the success of this approach is that HRP needs to be deactivated at the end of each analysis cycle, so that it will not generate false positive signals in the next cycle. To explore whether TCEP can deactivate HRP and cleave the fluorophores simultaneously, the inventors stained proteins ILF3 (FIG. 3A), HMGB1, HDAC2, TDP43, PABPN1, hnRNP A1 H4K16ac, hnRNP K, Nucleophosmin and Nucleolin (FIGS. 14-15) in HeLa cells using HRP-conjugated antibodies and tyramide-$N_3$-Cy5. After fluorophore cleavage with TCEP at 50° C. for 30 minutes, the fluorescence signals were efficiently removed, yielding the on/off ratios of over 10:1 (FIGS. 3B, 3D, and FIGS. 14-15). The inventors then incubated the cells with tyramide-$N_3$-Cy5 again. For all the proteins under study, no further fluorescence signal increases were observed (FIGS. 3C, 3D, and FIGS. 14-15). These results confirm that the protein staining signals generated by CFT can be efficiently erased by TCEP, and also indicate that TCEP can deactivate HRP simultaneously.

Multiplexed In Situ Protein Profiling in HeLa Cells

Figure 4:
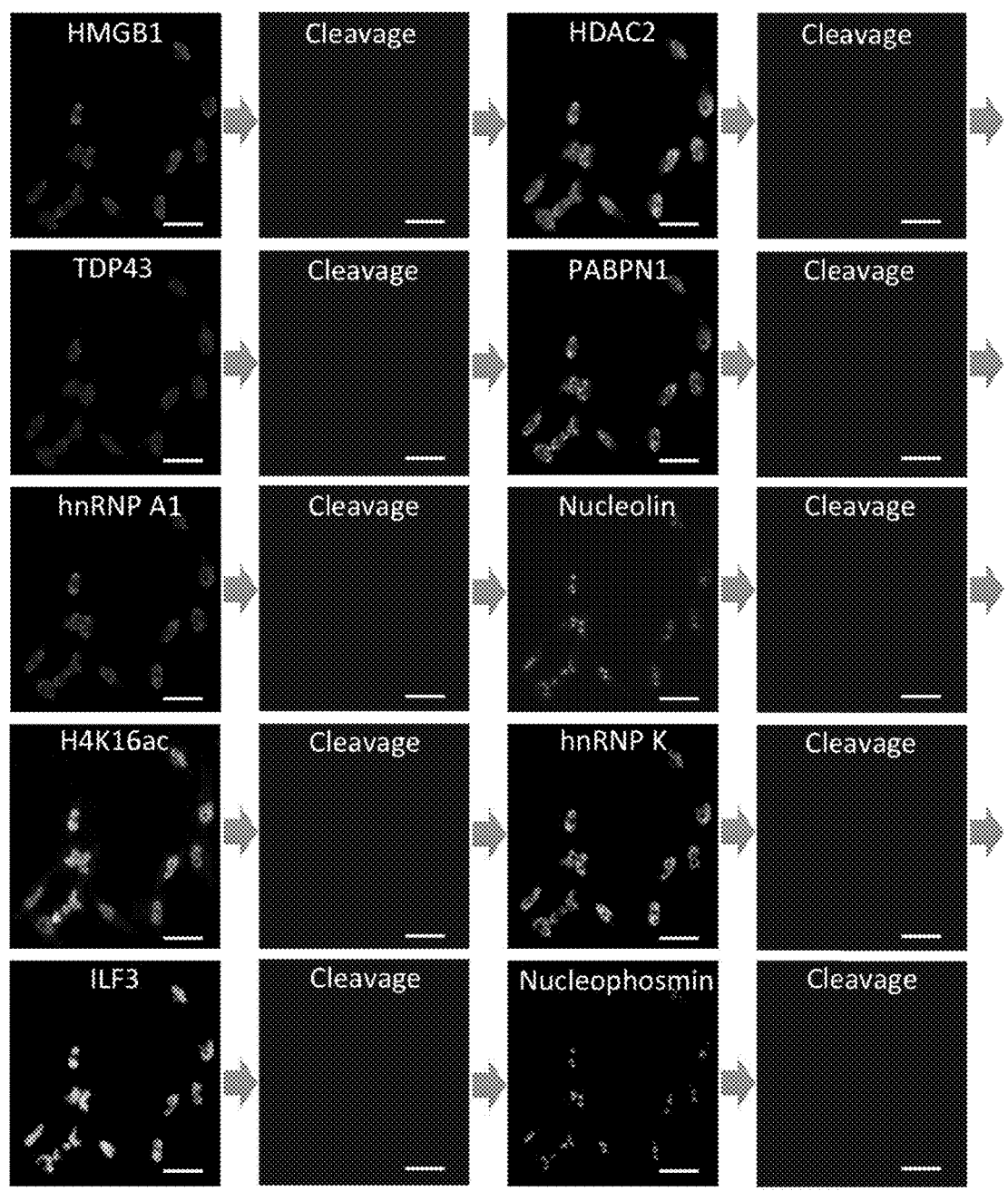
FIG. 4 shows 10 different proteins stained sequentially with the corresponding HRP conjugated antibodies and tyramide-$N_3$-Cy5 in the same set of HeLa cells. Scale bars, 40 μm.
Figures 5A, 5B:
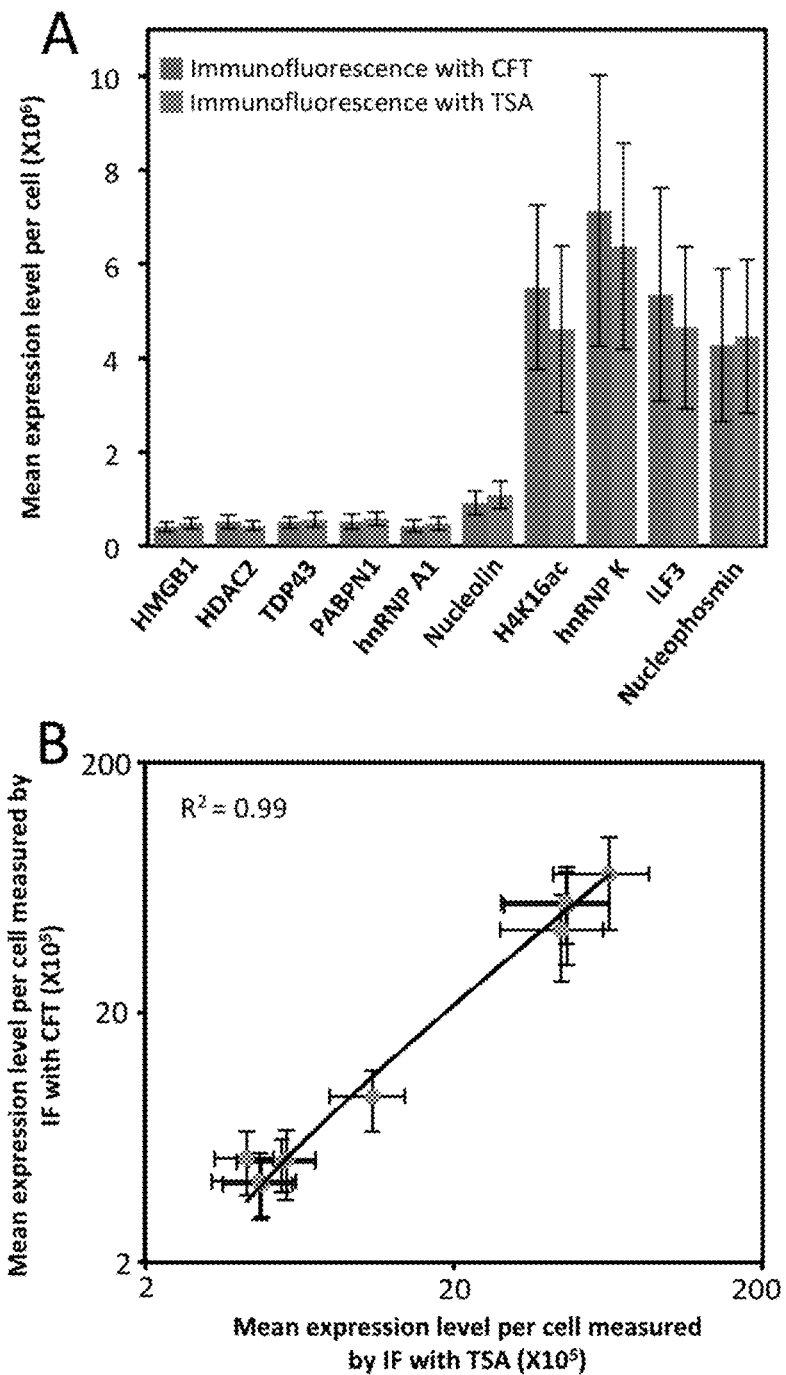
FIGS. 5A-5B. (A) Mean expression level per cell (n=200 cells) of 10 different proteins measured by immunofluorescence (IF) with cleavable fluorescent tyramide (CFT) and conventional immunofluorescence with tyramide signal amplification (TSA). (B) Comparison of the results obtained by immunofluorescence with CFT and TSA yields $R^2$=0.99 with a slope of 1.13. The x and y axes in (B) are on a logarithmic scale.
Figure 16:
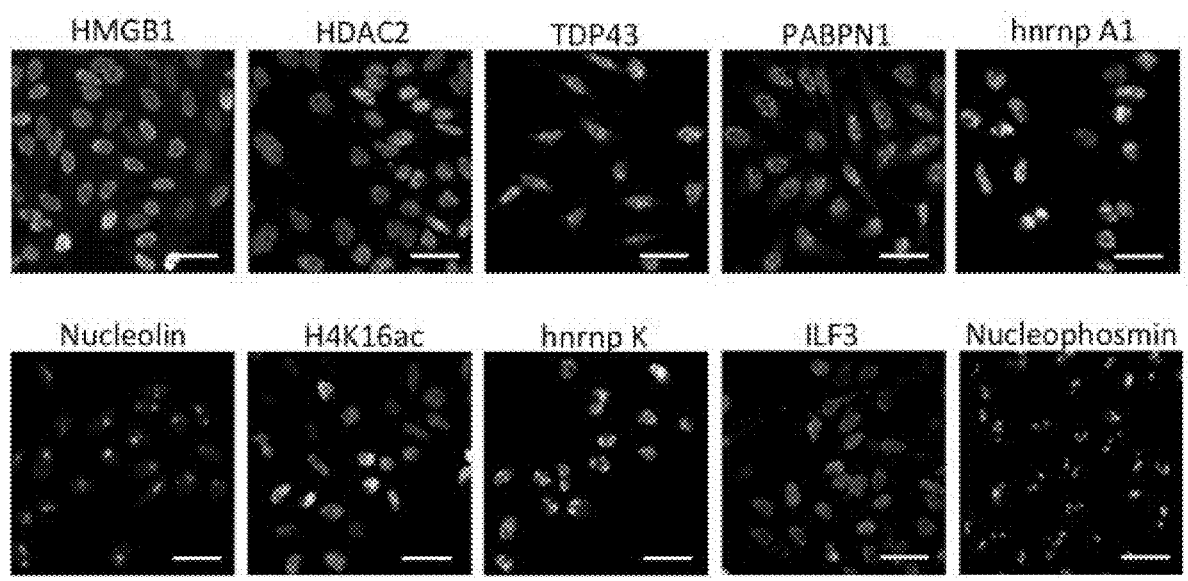
FIG. 16. 10 different proteins are stained with the corresponding HRP conjugated antibodies and Cy5 labeled tyramide in different HeLa cells. Scale bars, 40 μm.

To demonstrate the feasibility of applying CFT for multiplexed protein analysis, the inventors labeled 10 distinct proteins in individual HeLa cells in situ. Through reiterative staining cycles, proteins HMGB1, HDAC2, TDP43, PABPNF1, hnRNP A1, Nucleolin, H4K16ac, hnRNP K, ILF3 and Nucleophosmin were unambiguously detected with the HRP conjugated antibodies and tyramide-$N_3$-Cy5 in the same set of cells (FIG. 4). The inventors also stained these 10 protein targets in 10 different sets of cells by conventional tyramide signal amplification (TSA) assays using Cy5 labeled tyramide (FIG. 16). The protein distribution patterns obtained by the two methods are consistent with each other. The inventors also compared the mean protein abundances per cell measured by our CFT-based approach and conventional immunofluorescence with TSA. For all the 10 proteins with varied expression levels, the results obtained using the two methods closely resemble each other (FIG. 5A). Comparison of the two sets of results yields an $R^2$ value of 0.99 with a slope of 1.13 (FIG. 5B). These results indicate that our approach allows quantitative and multiplexed protein profiling in individual cells in situ.

Protein Expression Heterogeneity and Correlation

Figure 6A:
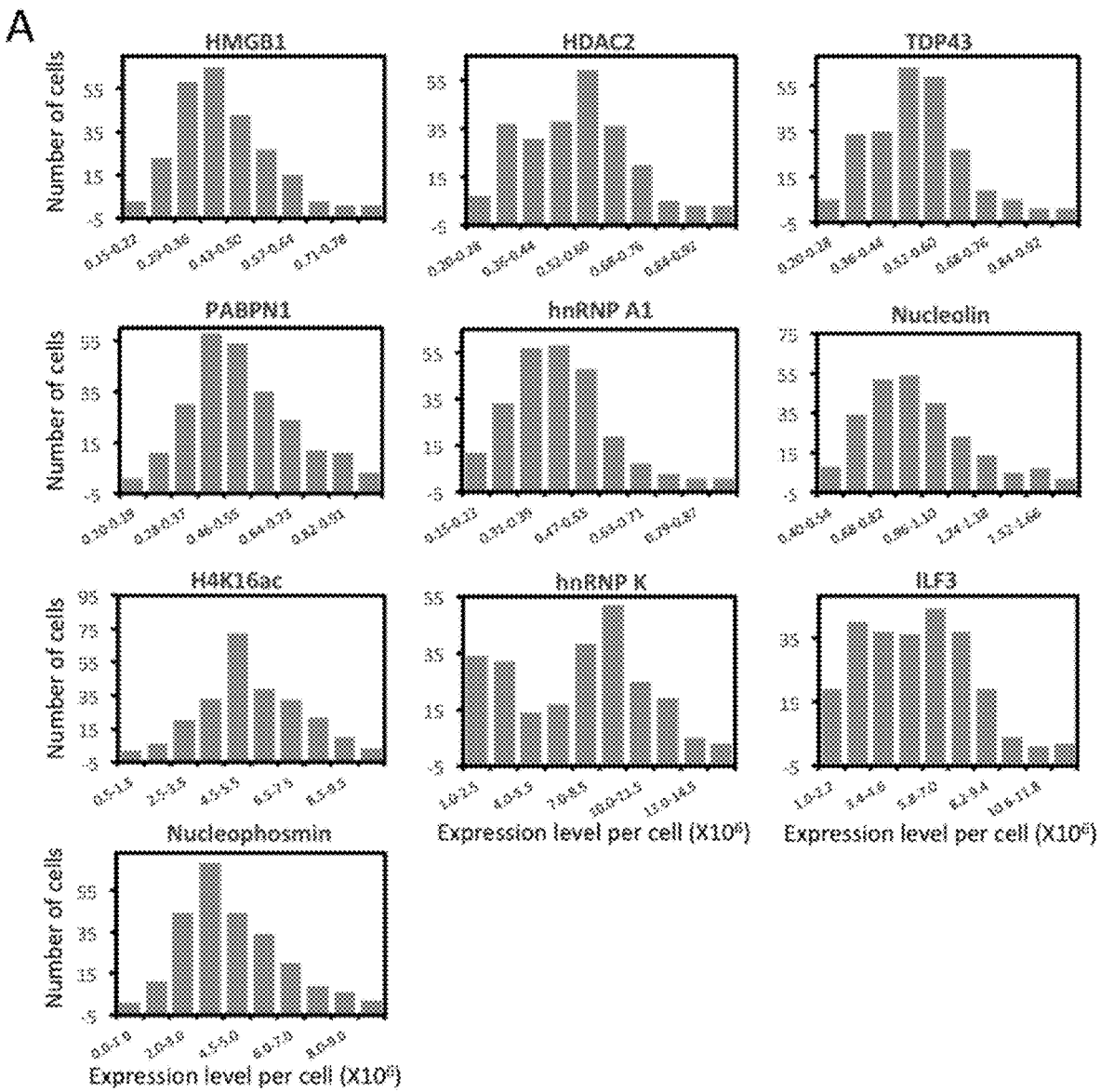
FIGS. 6A-6B. Protein expression heterogeneity and correlation. (A) Histograms of the expression level per cell of the 10 measured proteins. (B) Correlation of the expression levels of the 10 measured proteins and the hierarchical clustering tree. The upper triangle shows the expression correlation coefficient of each protein pair. The lower triangle displays the color corresponding to the correlation coefficient. Protein names are shown in the diagonal. A group of proteins identified by a threshold on the cluster tree (dashed line) is indicated by the black box in the matrix and the red lines on the tree.

As shown in many experiments, genetically identical cells can exhibit significant gene expression variations among individual cells. To explore such cell-to-cell protein expression heterogeneity in HeLa cells, the inventors analyzed the distribution of the single-cell protein expression levels. As shown in FIG. 6A, the single-cell protein abundances are distributed in a wide range. This significant expression heterogeneity results in the relatively large error bars in FIG. 7. For all the ten measured proteins, the square of the expression standard deviation is much higher than the mean expression levels (FIG. 6A). These results suggest that these proteins are generated in translational bursts, rather than at a constant rate.

Figure 6B:
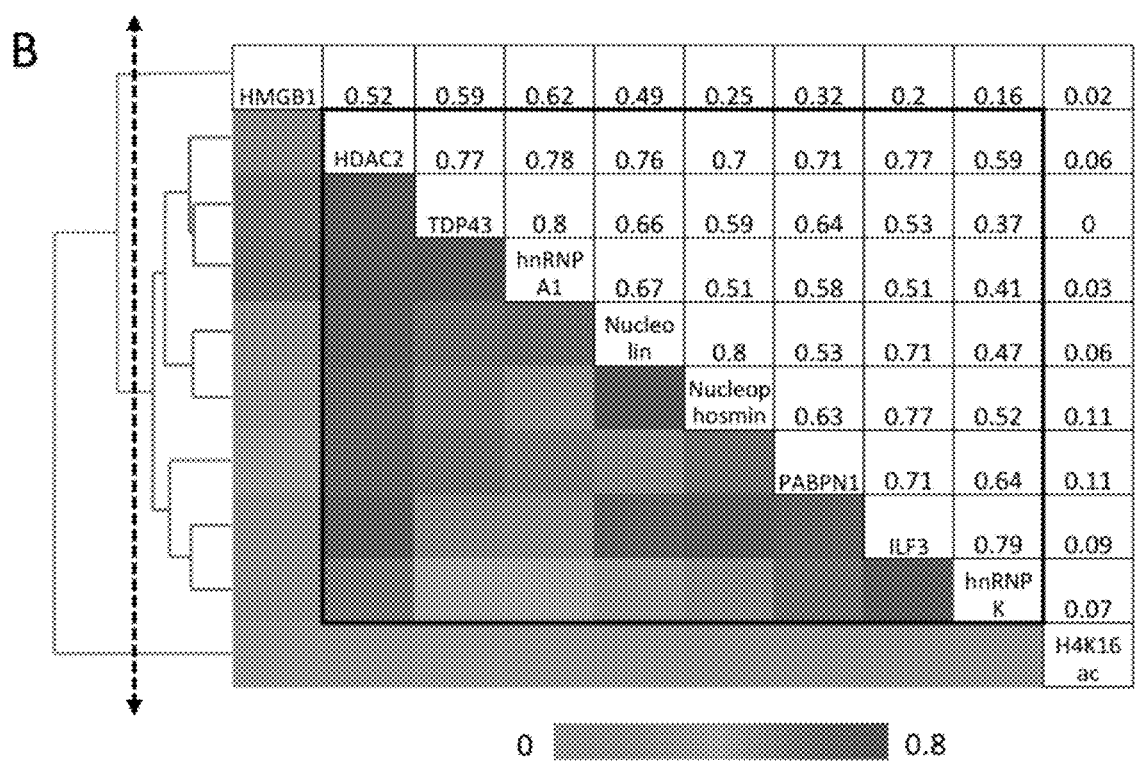
Figure 17:
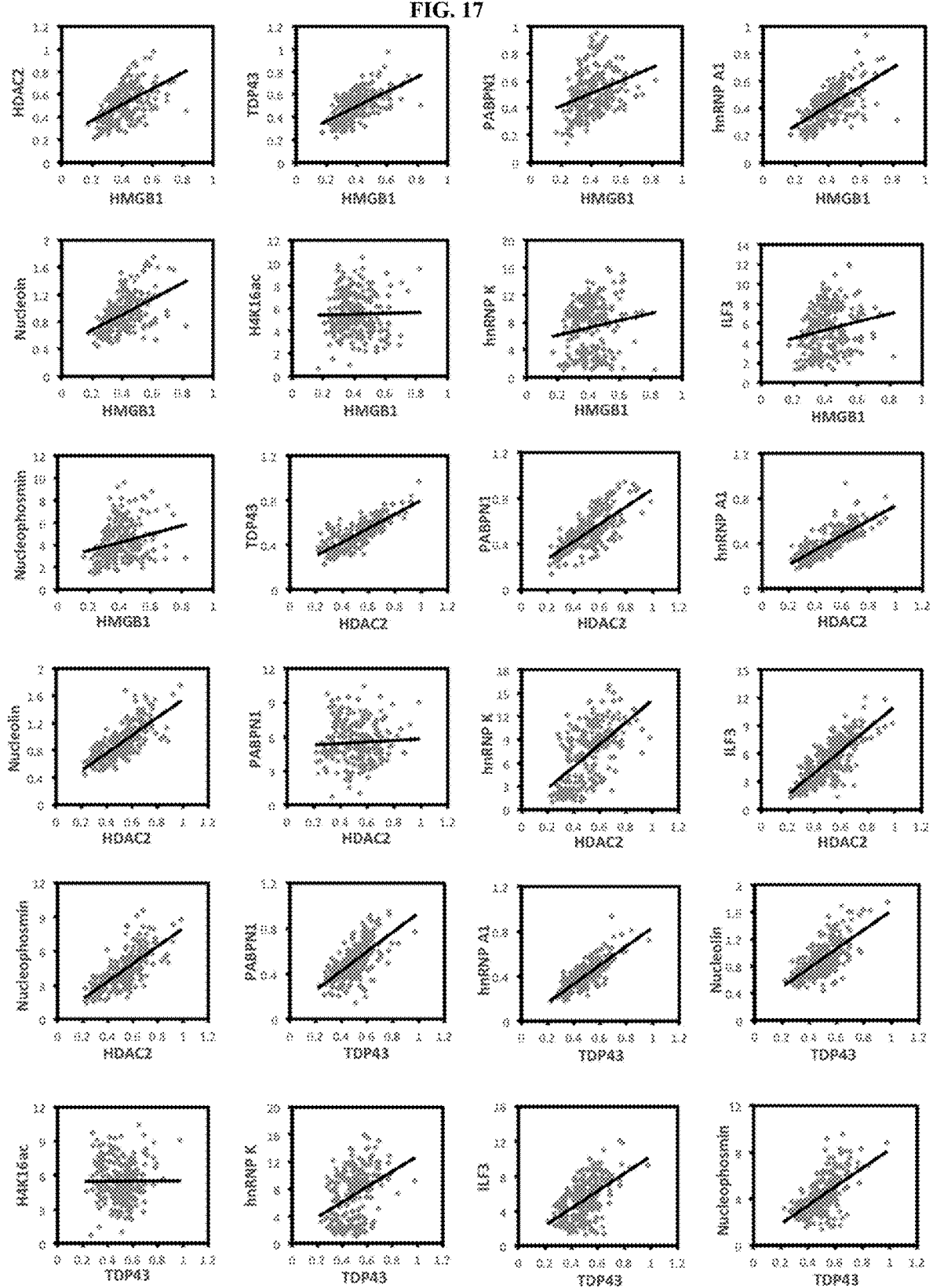
FIG. 17 shows raw expression correlation data of each gene pair. Each spot corresponds to one cell with expression levels in the x and y axes ($\times 10^6$).
Figure 18:
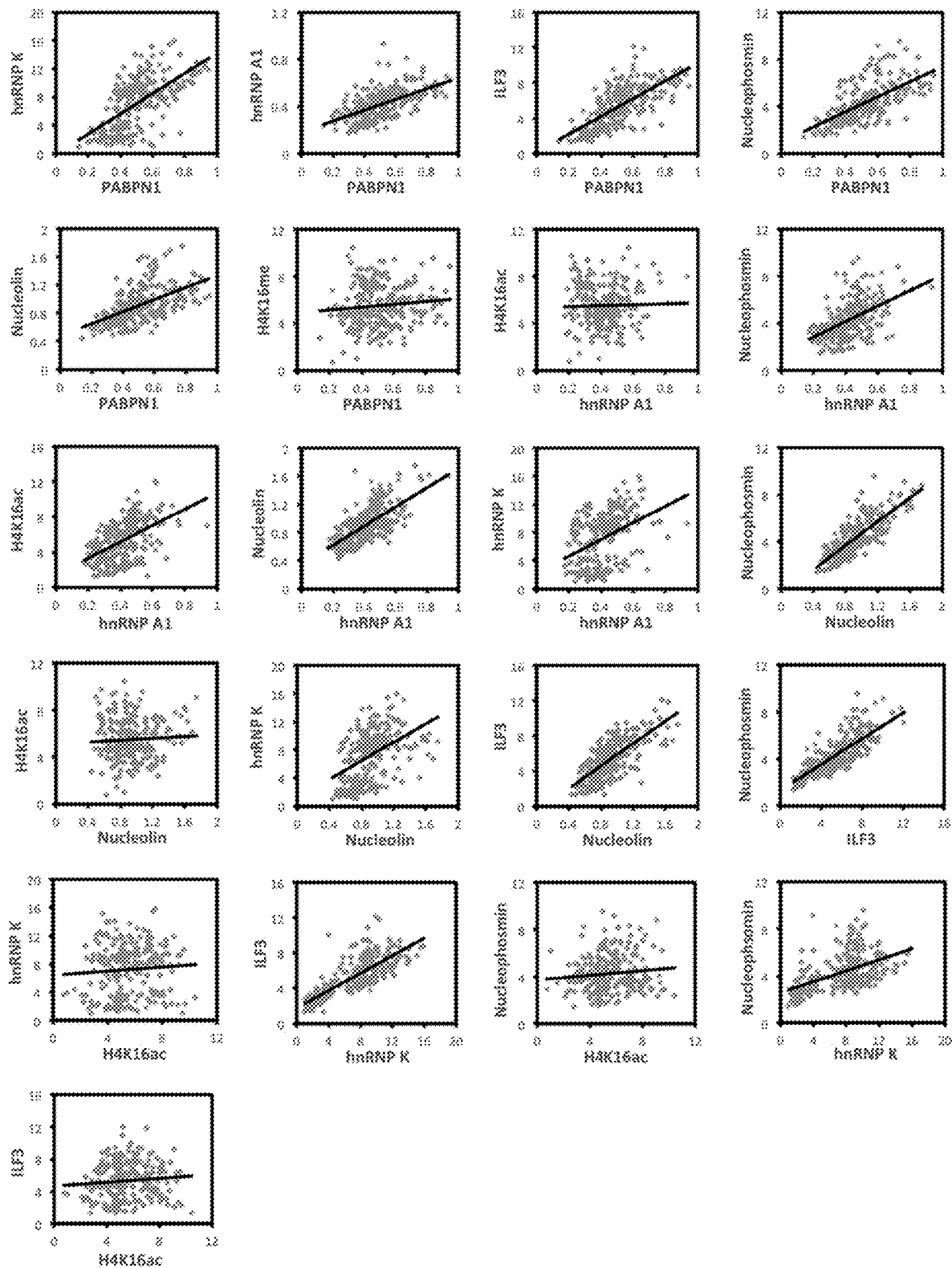
FIG. 18 shows raw expression correlation data of each gene pair. Each spot corresponds to one cell with expression levels in the x and y axes ($\times 10^6$).

By analyzing expression covariation of different proteins, one can study which proteins are co-regulated to elucidate their regulatory pathways. For bulk cell analysis, such studies usually require external stimuli to introduce varied gene expression among different cell populations. At the single-cell level, stochastic gene expression variation is generated in individual cells. By taking advantage of this natural expression fluctuation, one can perform single cell expression covariation analysis to refine existing regulatory pathways, suggest new regulatory pathways, and predict the function of unannotated proteins. Appling this approach, the inventors studied the pairwise expression correlation of the ten measured proteins (FIGS. 17-18), and calculated the correlation coefficient of each protein pair (FIG. 6B). Some of protein pairs show highly correlated covariation with correlation coefficients of ~0.8, such as TDP43 and hnRNP A1 along with Nucleolin and Nucleophosmin. To further explore the regulatory network among the measured proteins, the inventors adopted a hierarchical clustering approach (FIG. 6B). On the generated cluster tree, the inventors identified a group of eight proteins with substantially correlated expression patterns (FIG. 6B). Indeed, all the eight proteins in this identified group are involved in the transcriptional regulation and processing related pathways.

Multiplexed In Situ Protein Profiling in FFPE Human Hippocampus

The various cell types in the brain cooperate collectively to achieve high-order mental functions. To accurately observe and precisely manipulate brain activities, it is required to have much greater knowledge of the molecular identities of specific cell types. This knowledge is also fundamental to the discovery of the cell-type targeted therapy to treat brain disorders. The identities of neurons are determined by their locations, protein, RNA, and DNA profiles, etc. However, the current molecular classification of human neurons is only defined by single-cell RNA-seq. No systematic analysis of neuronal heterogeneity has been reported based on protein expression or molecular profiling in their natural spatial contexts. Additionally, FFPE postmortem tissues are the major source of human brains with unlimited regional sampling and depth. However, the limited sensitivity of the existing multiplexed in situ protein analysis methods hinders their applications to profile the partially degraded proteins in highly autofluorescent FFPE tissues.

Figure 7:
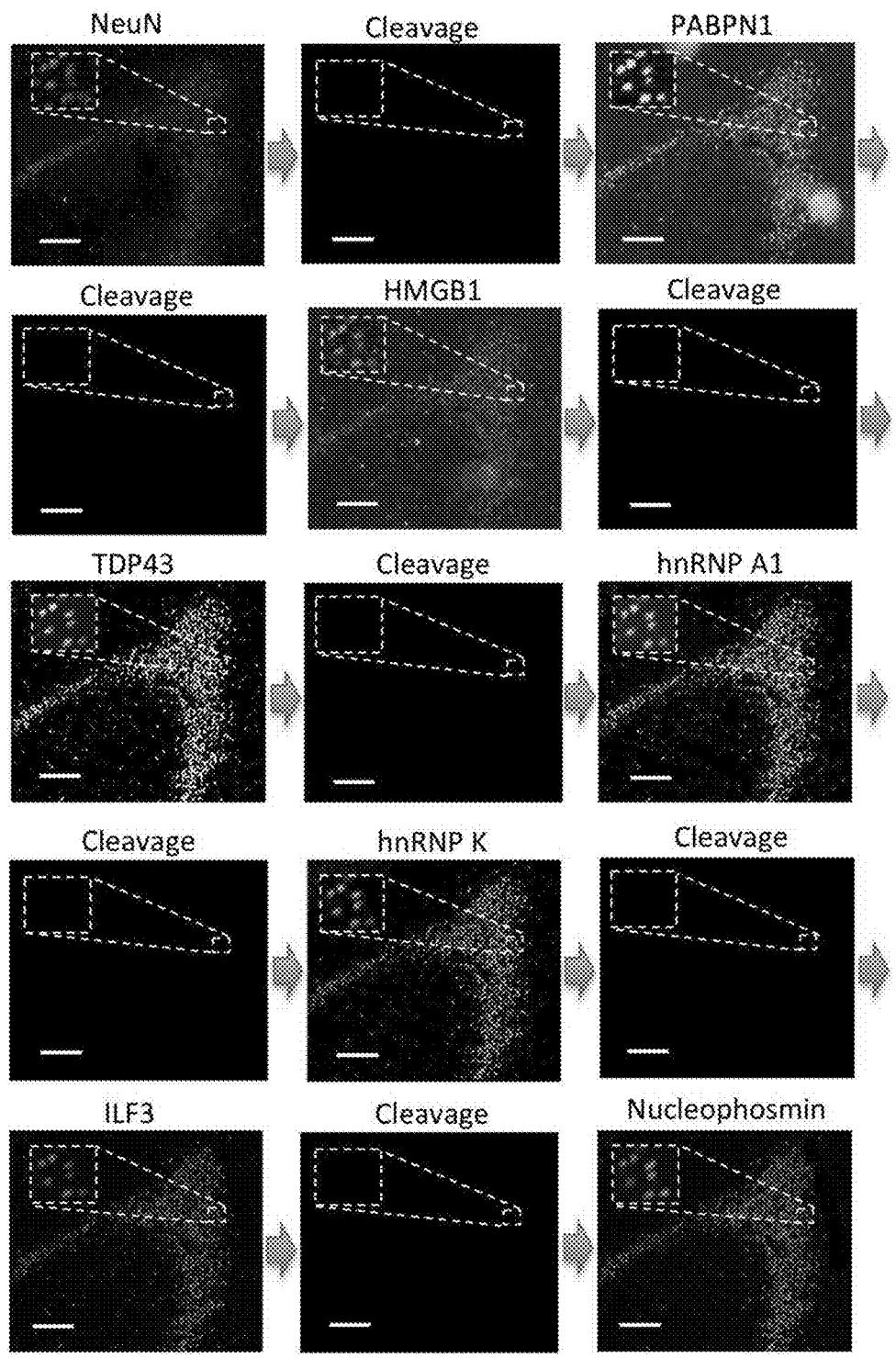
FIG. 7 shows sequential detection of eight different proteins using HRP conjugated antibodies and tyramide-$N_3$-Cy5 in FFPE human brain tissue. Scale bars, 200 μm.

To explore the human neuronal heterogeneity by multiplexed in situ protein profiling and also to assess the feasibility of applying CFT for analyzing FFPE tissues, the inventors stained 8 proteins sequentially in the human hippocampus using HRP conjugated antibodies and tyramide-$N_3$-Cy5. Of the 8 proteins, NeuN was selected as the neuronal marker, and PABPN1, HMGB1, TDP43, hnRNP A1, hnRNP K, ILF3 along with Nucleophosmin were selected as the components of the transcriptional regulation and processing pathways. Due to the high sensitivity of our approach, the imaging exposure time can be minimized without compromising the analysis accuracy. As a result, the whole tissue (~1 cm×1 cm) was imaged within 30 minutes in each cycle. With 8 reiterative staining cycles, all the measured proteins were successfully detected in the tissue (FIG. 7). These results suggest that our approach enables multiplexed single-cell in situ protein profiling in FFPE tissues with high sample throughput and short assay time.

Figures 8A, 8B:
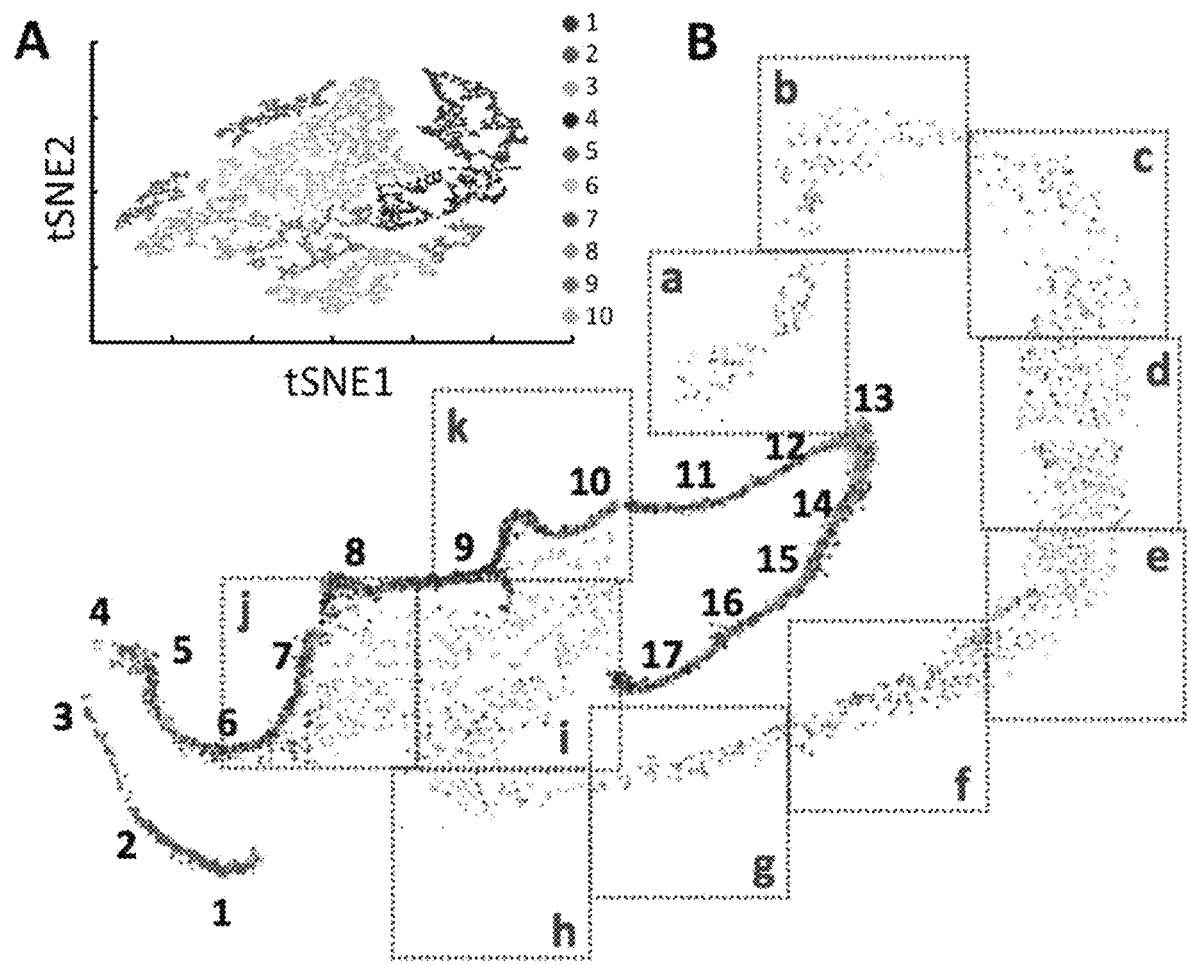
FIGS. 8A-8B. (A) Over 6000 neurons in a human hippocampus are partitioned into 10 clusters. (B) Anatomical locations of the individual neurons from the 10 clusters in the DG (1-17), CA1 (a-e), CA2 (f), CA3 (g,h) and CA4 (i-k). Scale bars, 2 mm.
Figure 9:
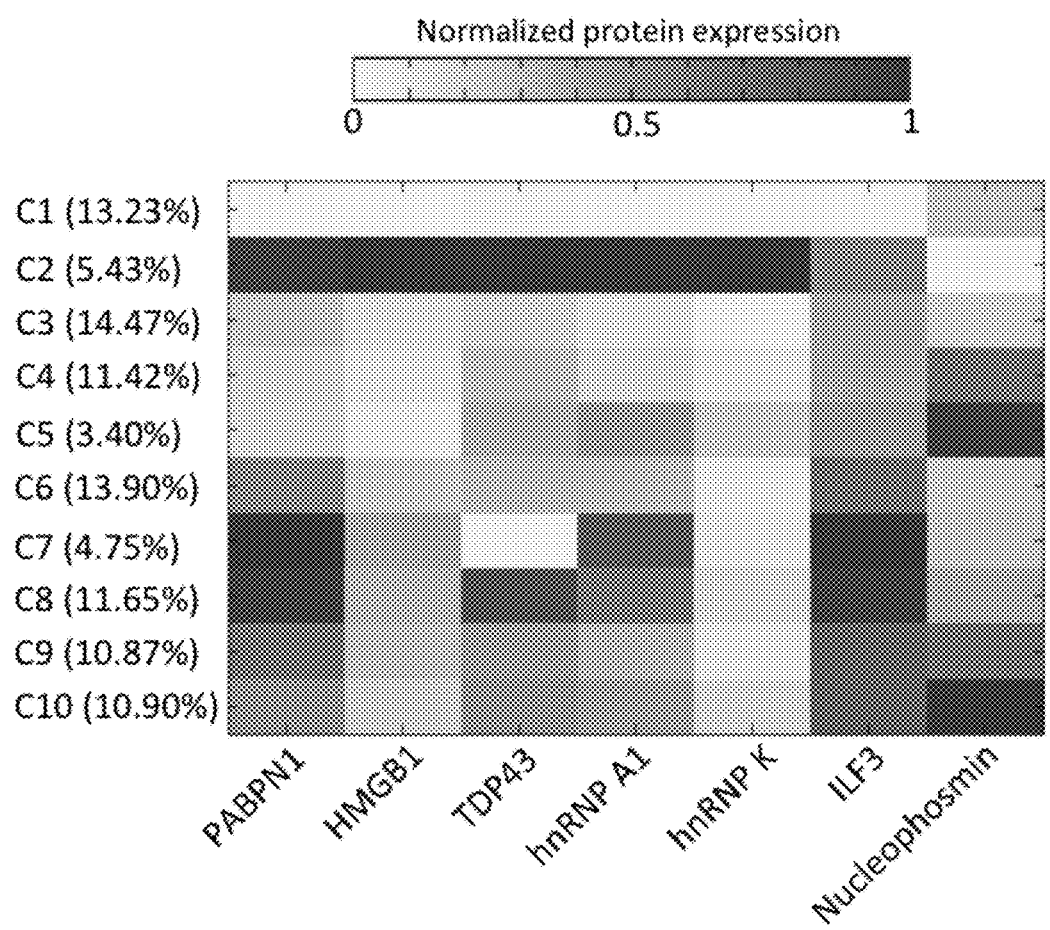
FIG. 9 shows distinct protein expression patterns in the 10 cell clusters and the percentage of cells in each cluster.
Figures 10A, 10B:
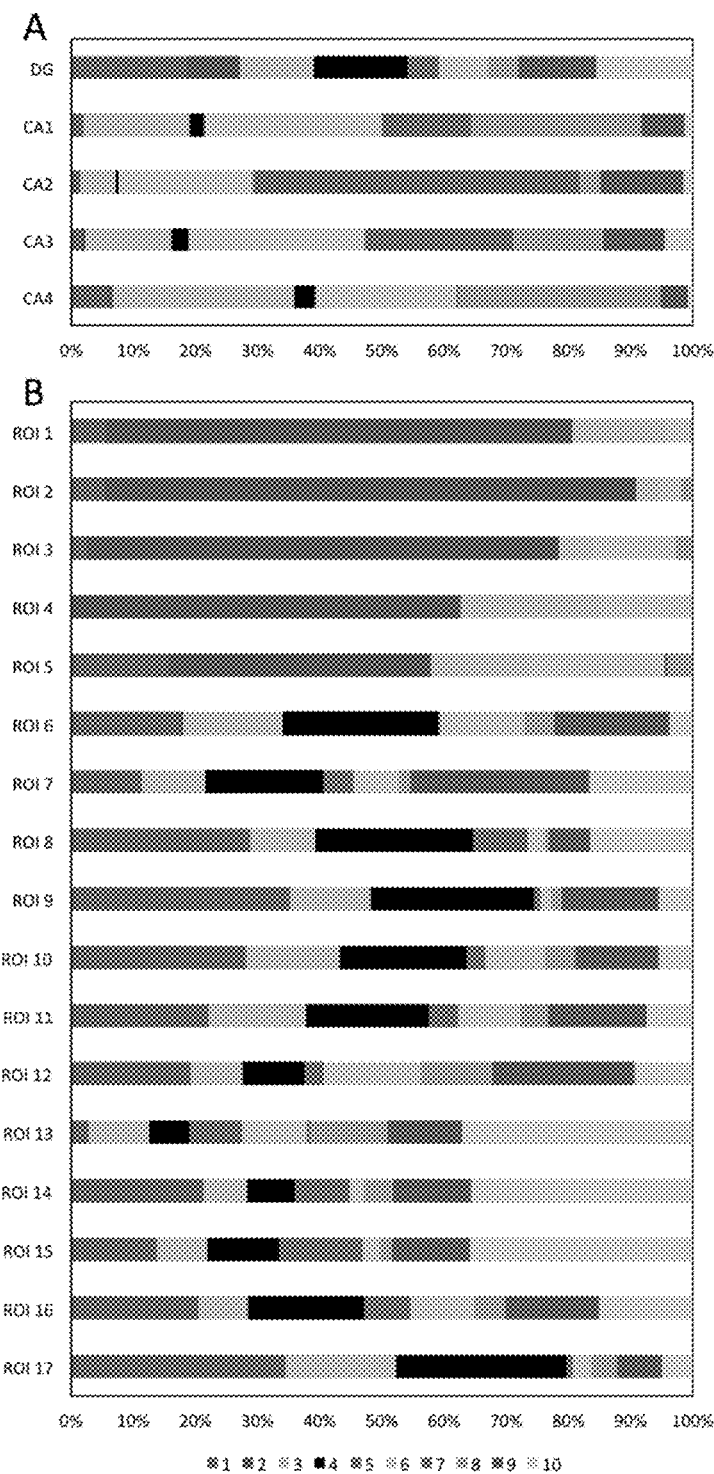
FIGS. 10A-10B. (A) The DG and CA fields are composed of neurons from different cell clusters. (B) Varied ROI in the DG are composed of neurons from different cell clusters.
Figures 12A, 12B, 12C, 12D, 12E:
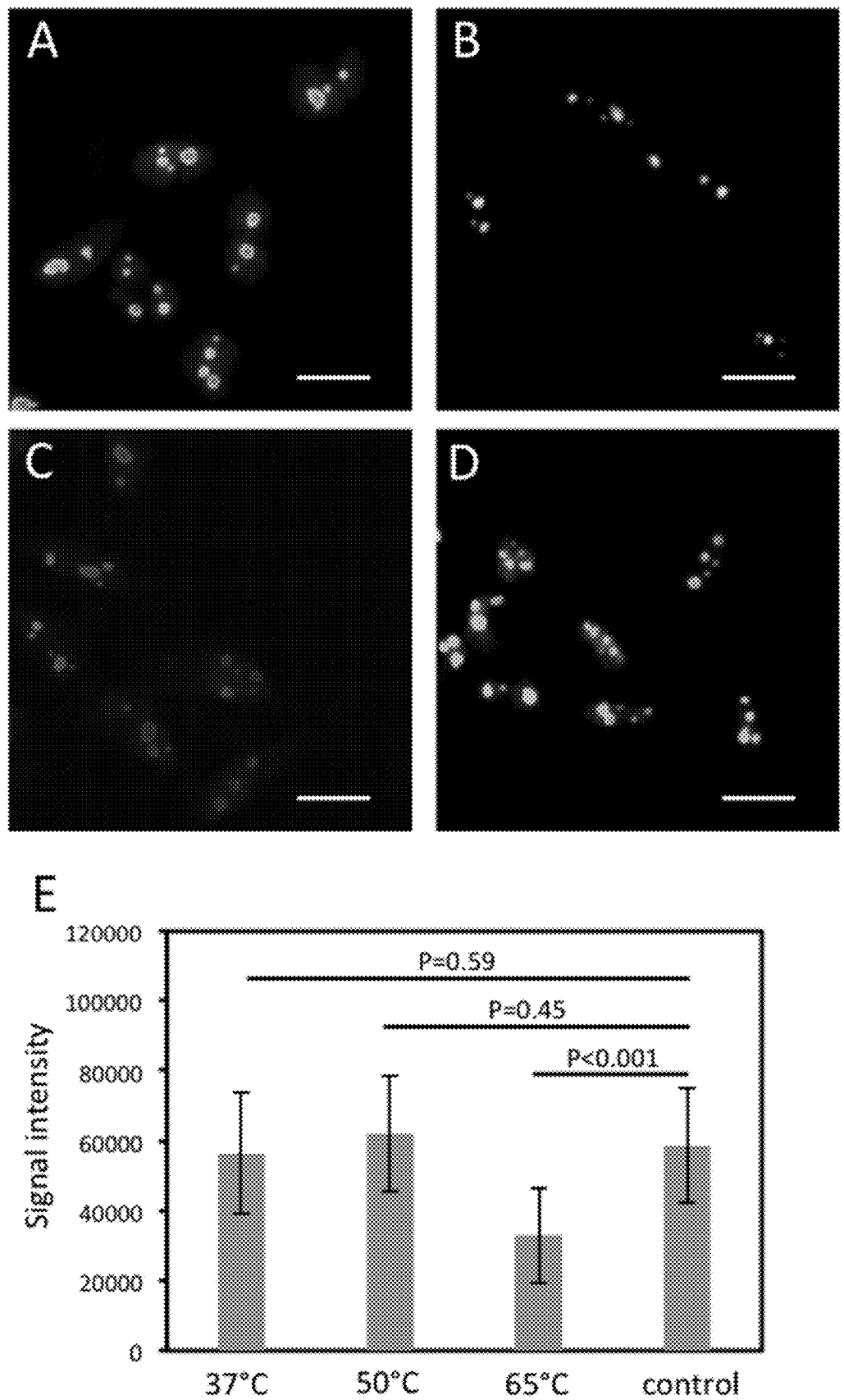
FIGS. 12A-12E. After incubation with TCEP at (A) 37° C., (B) 50° C. and (C) 65° C. for 24 hours, or (D) without any TCEP pre-treatment, protein Ki67 in HeLa cells is stained with tyramide-$N_3$-Cy5. (E) The obtained signal intensities with TCEP pretreatment at different temperatures and without any pre-treatment (control) (n=30 positions). Scale bars, 20 μm.
Figures 13A, 13B, 13C, 13D, 13E, 13F, 13G, 13H, 13I, 13J, 13K, 13L, 13M:
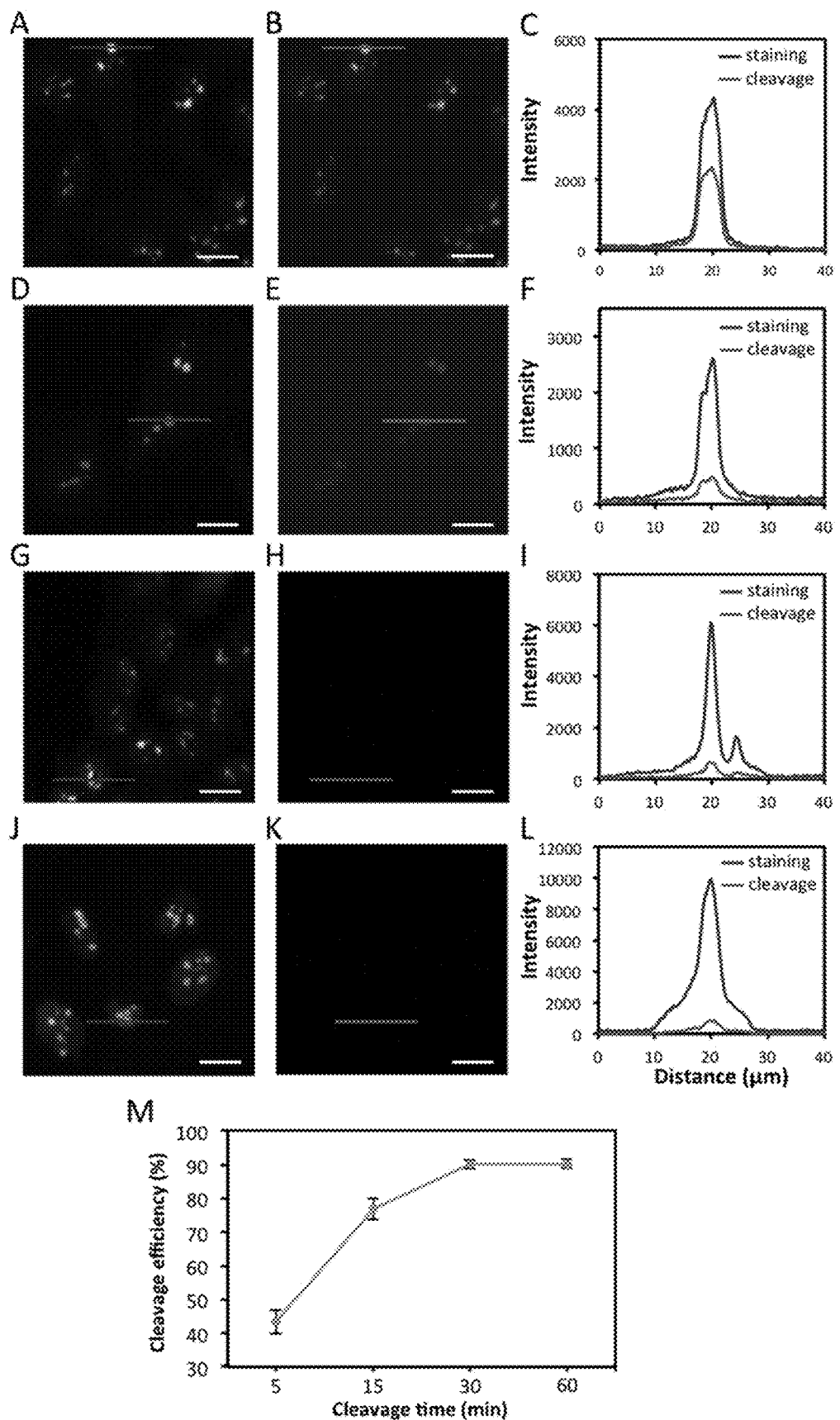
FIGS. 13A-13M. (A) Protein Ki67 in HeLa cells is stained with tyramide-$N_3$-Cy5. (B) The stained cells are incubated with TCEP at 50° C. for 5 minutes. (C) Fluorescence intensity profile corresponding to the red line and green line positions in (A) and (B). (D) Protein Ki67 in HeLa cells is stained with tyramide-$N_3$-Cy5. (E) The stained cells are incubated with TCEP at 50° C. for 15 minutes. (F) Fluorescence intensity profile corresponding to the red line and green line positions in (D) and (E). (G) Protein Ki67 in HeLa cells is stained with tyramide-$N_3$-Cy5. (H) The stained cells are incubated with TCEP at 50° C. for 30 minutes. (I) Fluorescence intensity profile corresponding to the red line and green line positions in (G) and (H). (J) Protein Ki67 in HeLa cells is stained with tyramide-$N_3$-Cy5. (K) The stained cells are incubated with TCEP at 50° C. for 60 minutes. (L) Fluorescence intensity profile corresponding to the red line and green line positions in (J) and (K). (M) Fluorophore cleavage efficiency at different reaction time (n=30 positions). Scale bars, 20 μm.
Figure 14:
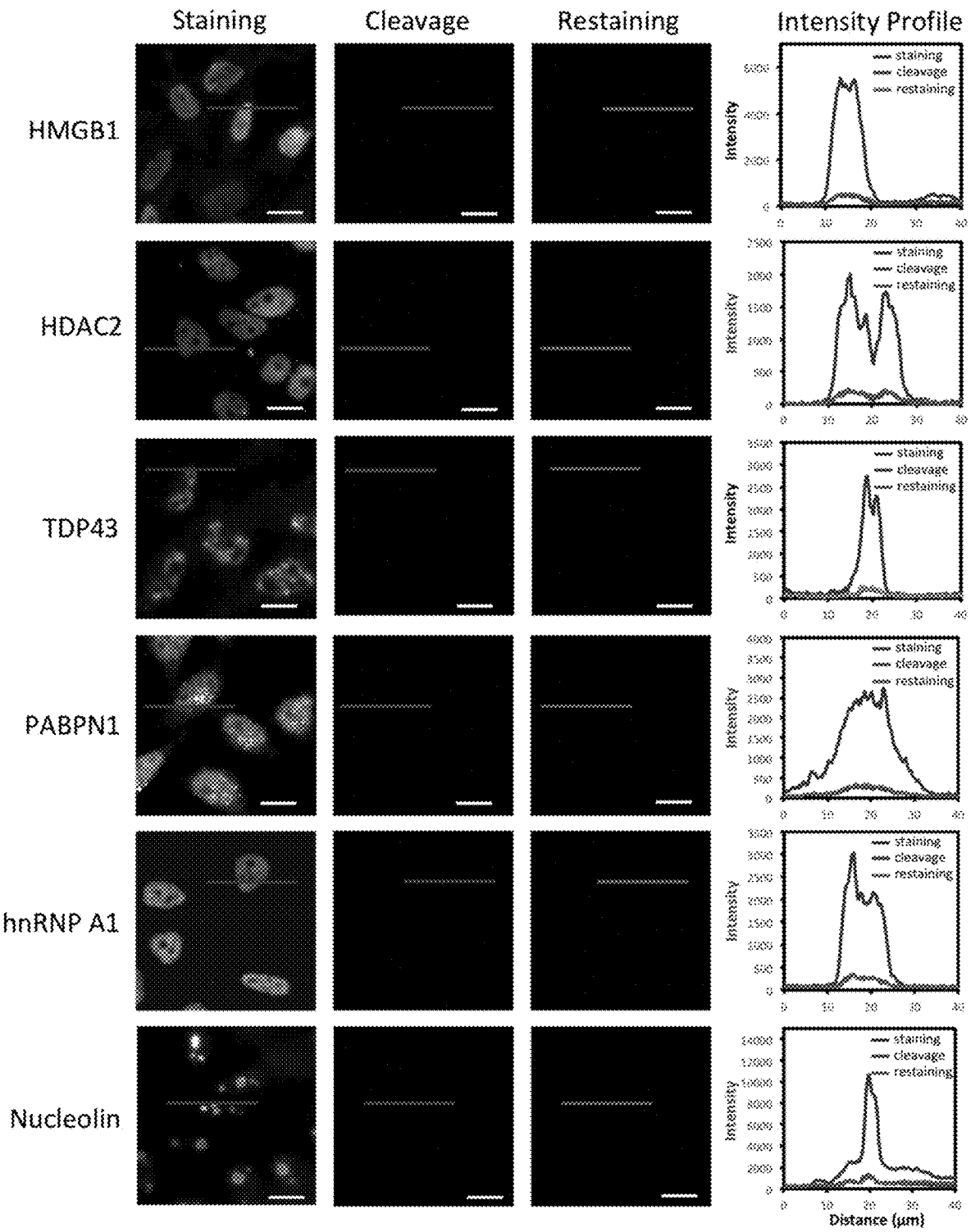
FIG. 14. Different proteins in HeLa cells are stained with HRP conjugated antibodies and tyramide-$N_3$-Cy5 (the first column). The stained cells are incubated with TCEP (the second column). Subsequently, the cells are incubated with tyramide-$N_3$-Cy5, again (the third column). Fluorescence intensity profiles corresponding to the red, blue and green line positions in the staining, cleavage and restaining images (the fourth column). Scale bars, 15 μm.
Figure 15:
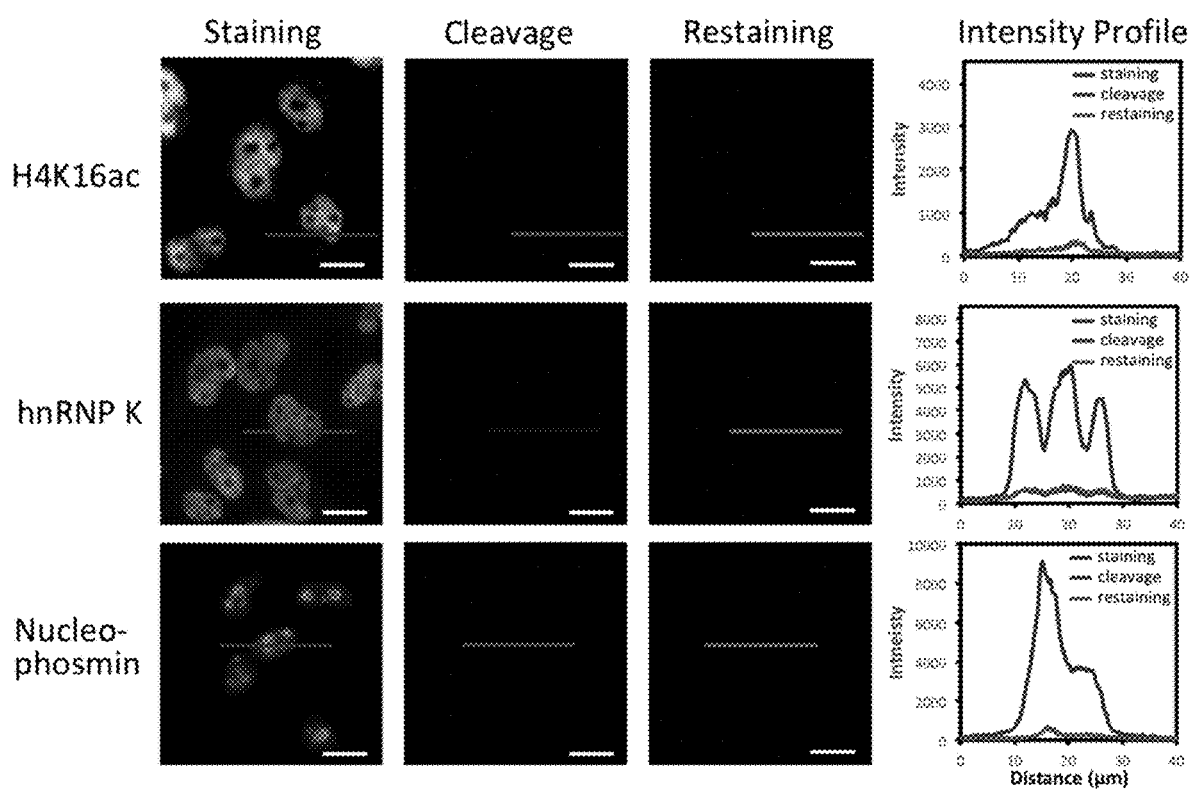
FIG. 15. Different proteins in HeLa cells are stained with HRP conjugated antibodies and tyramide-$N_3$-Cy5 (the first column). The stained cells are incubated with TCEP (the second column). Subsequently, the cells are incubated with tyramide-$N_3$-Cy5, again (the third column). Fluorescence intensity profiles corresponding to the red, blue and green line positions in the staining, cleavage and restaining images (the fourth column). Scale bars, 15 μm.
Figure 19:
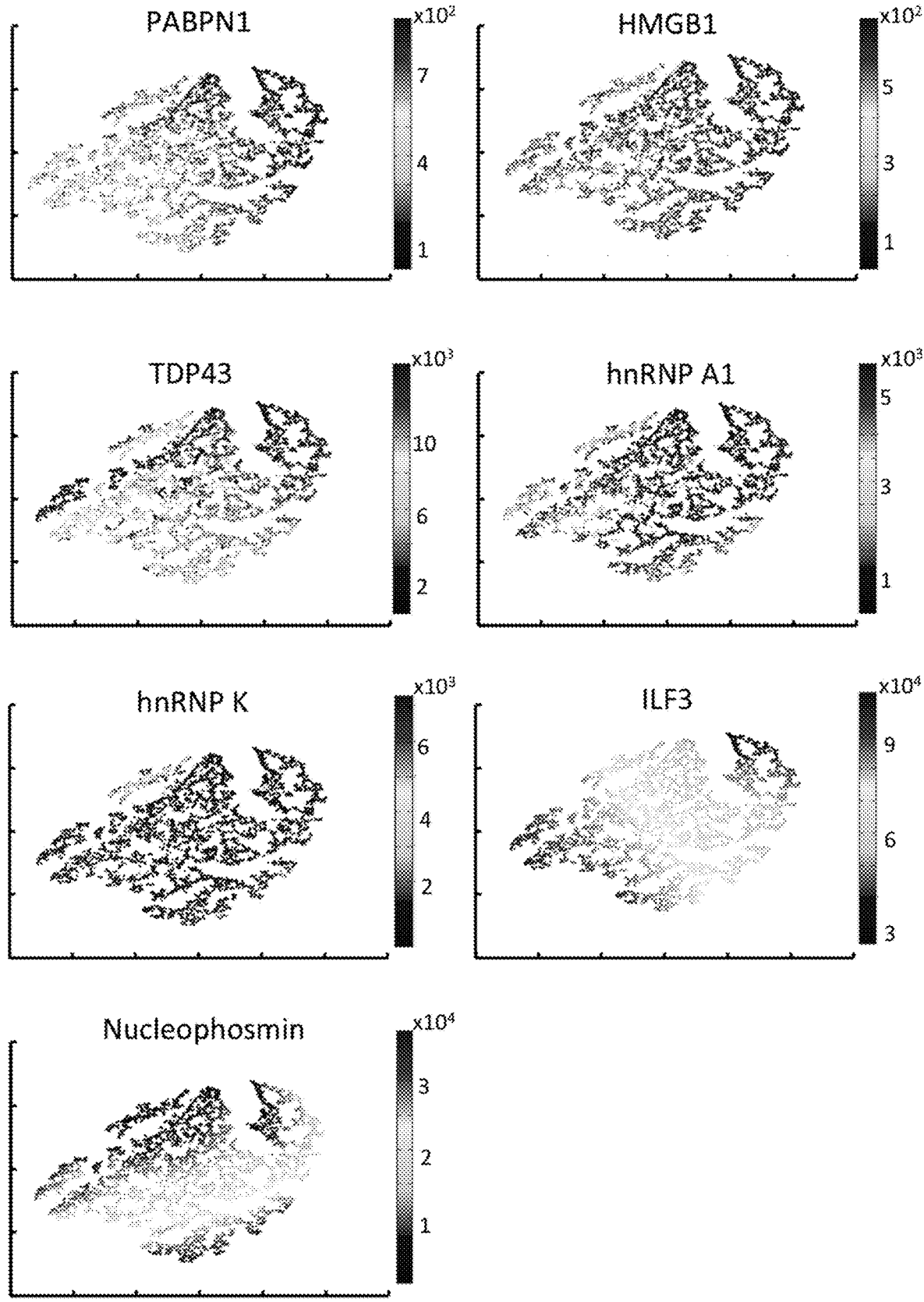
FIG. 19 demonstrates distribution of single-cell protein expression in viSNE plots.
Figure 20:
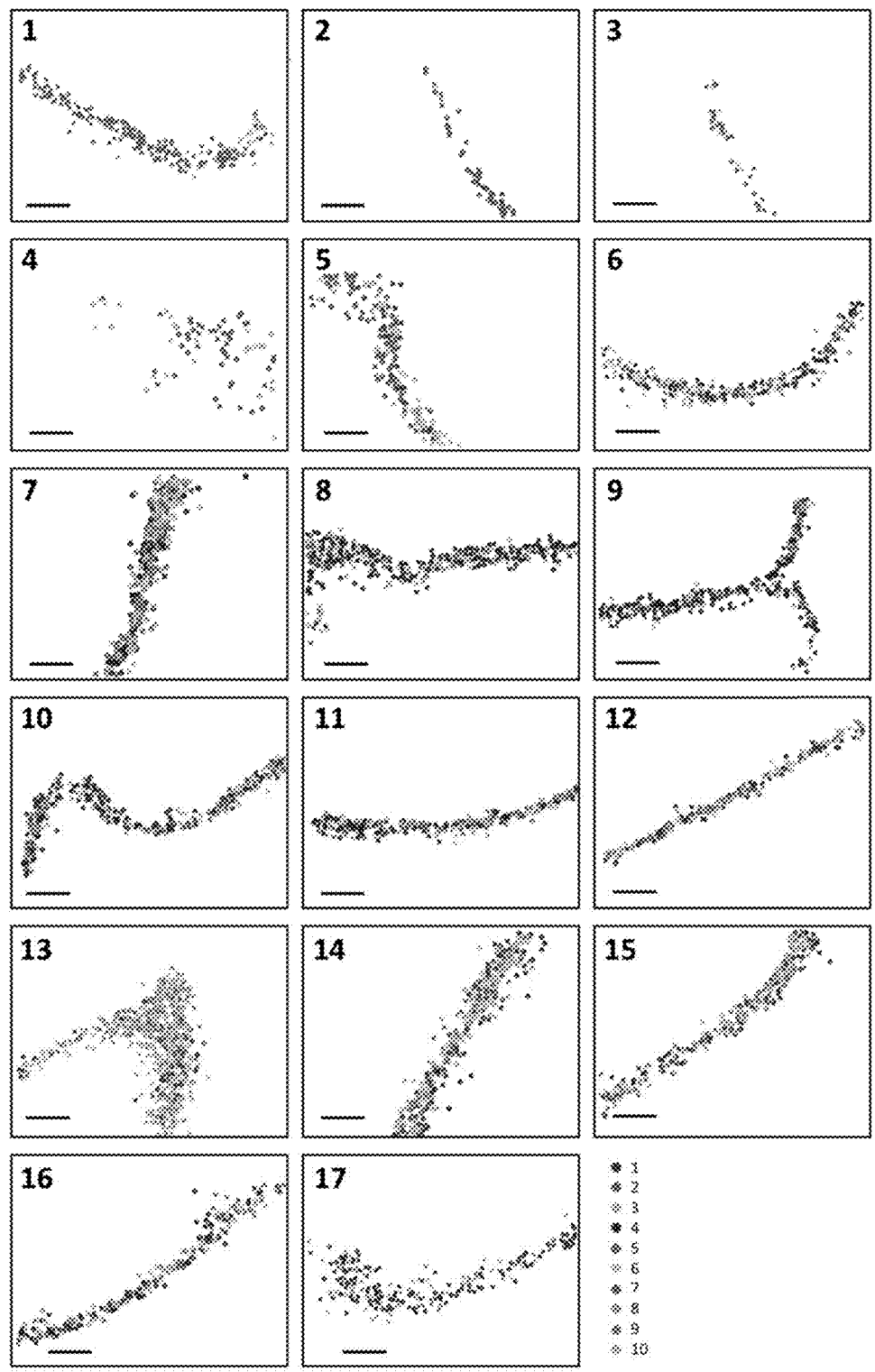
FIG. 20. Zoom-in views of different regions of interest (ROI) in the dentate gyrus (DG) in FIG. 8B. Scale bars, 200 μm.
Figure 21:
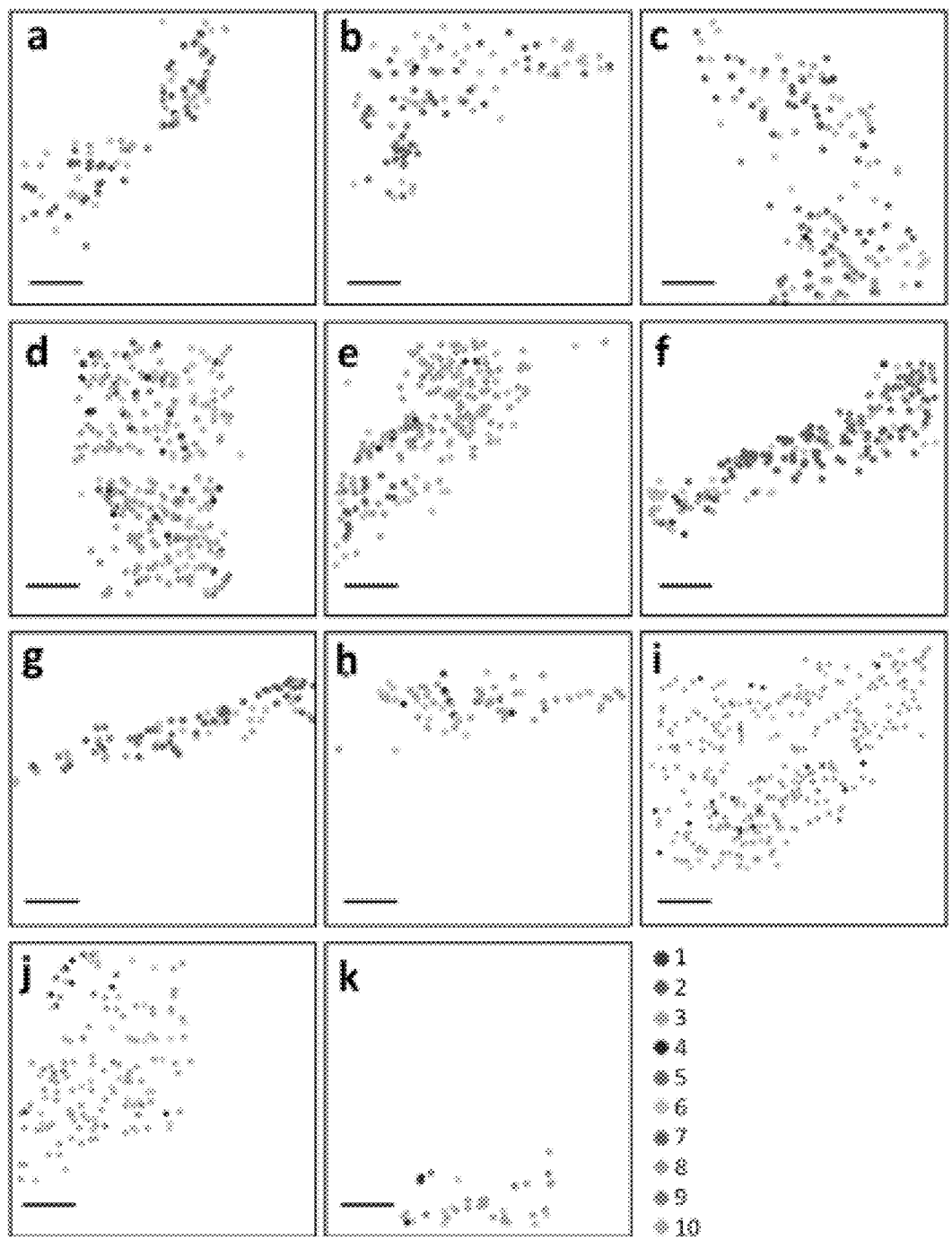
FIG. 21. Zoom-in views of different ROI in the Cornu Ammonis (CA) fields in FIG. 8B. Scale bars, 500 μm.

With the multiplexed single-cell in situ protein profiling results, the inventors explored the neuronal heterogeneity and their spatial organization in the human hippocampus. In the examined tissue, protein expression levels were calculated in >6000 individual neurons, which were identified by the neuronal marker NeuN. Next, the software viSNE was applied to partition the individual neurons into 10 clusters (FIG. 8A) based on their protein expression profiles (FIG. 9, FIG. 19). By mapping these 10 clusters of cells back to their natural locations in the tissue (FIG. 8B, FIGS. 20-21), the inventors observed that different subregions of the hippocampus consist of neurons from distinct clusters. For example, the dentate gyms (DG) contains all the clusters except cluster 7, while the Cornu Ammonis (CA) fields are dominated by clusters 3, 6, 7, and 8. Within the CA fields, cluster 7 only appears in CA1, CA2 and CA3, but not in CA4 (FIG. 10A). In the DG, cluster 2 is the major cell class in the regions of interest (ROI) 1-5. In contrast, other subregions of the DG are mainly composed of clusters 1, 3, 4, 9 and 10 (FIG. 10B). These results suggest that this approach allows the investigation of the different cell type compositions and their spatial organizations in FFPE tissues.

Discussion

In summary, the inventors have designed and synthesized cleavable fluorescent tyramide, and applied it for multiplexed protein profiling in single cells of FFPE tissues in situ. Compared with the existing multiplexed protein imaging technologies, our approach has enhanced the detection sensitivity by 1-2 orders of magnitude. Additionally, by minimizing the imaging time and avoiding the pixel-by-pixel data acquisition, our method enables the whole-slide scanning within 30 minutes, which dramatically increases the sample throughput and reduces the assay time. Applying our approach, we have shown that different subregions of the human hippocampus consist of varied neuron clusters. Interestingly, these distinct clusters are defined only on the basis of the protein expression profiles, without incorporating the cellular spatial information into the clustering algorithm.

These results suggest that the varied activity patterns and different microenvironment may contribute to the neuronal heterogeneity in the human hippocampus.

Figures 22A, 22B:
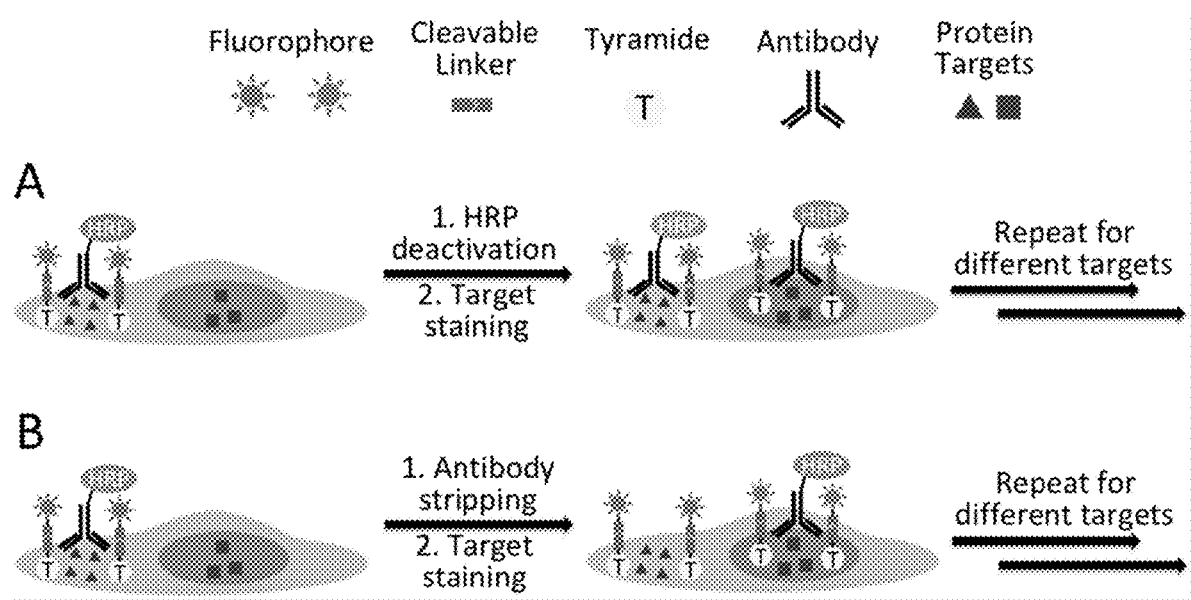
FIGS. 22A-22B. (A) Through reiterative HRP deactivation or (B) cyclic antibody stripping, multiple protein targets can be detected in each analysis cycle using CFT with different fluorophore.

The multiplexing capacity of this in situ protein profiling approach depends on two factors: the cycling number and the number of proteins interrogated in each cycle. TCEP can efficiently remove the fluorophores within 30 minutes, while the antigenicity of protein targets is preserved after incubation with TCEP for more than 24 hours. These results suggest that at least ~50 cycles can be carried out in one specimen. Coupled with the various established antibody stripping methods or HRP inactivation methods, our approach will enable four or five different protein targets to be profiled in each analysis cycle using CFT with distinct fluorophores (FIG. 22). Therefore, this CFT-based approach has the potential to detect hundreds of protein targets in the same tissue.

The cleavable fluorescent tyramide developed here can also be applied in other areas beyond protein analysis, such as DNA or RNA in situ hybridization and metabolic analysis. The combination of these applications will enable the integrated DNA, RNA, protein and metabolic analysis at the optical resolution in intact tissues. Furthermore, coupled with a program-controlled microfluidic system, a standard fluorescence microscope can be easily converted into an automatic highly multiplexed tissue imaging system. This comprehensive molecular imaging platform will bring new insights into cell signaling regulation, cell heterogeneity, cellular microenvironment, molecular diagnosis and cellular targeted therapy.

Example 2: Synthesis of tyramide-N$_3$-Cy5

Chemicals and solvents were purchased from Sigma-Aldrich or TCI America and were used directly without further purification, unless otherwise noted. Bioreagents were purchased from Invitrogen, unless otherwise indicated. $^1$H-NMR and $^{13}$C-NMR were taken on Varian Innova 400 MHz NMR spectrometers. Chemical shifts are reported in parts per million (ppm) downfield from tetramethylsilane (TMS). Data are reported as follows: chemical shift, multiplicity: singlet (s), doublet (d), triplet (t), multiplet (m), coupling constants J in Hz, and integration. FIRMS was performed by the Arizona State University mass spectrometry facility.

Scheme S1. Synthesis of tyramide-N$_3$-Cy5. Reagents and conditions: (i) N,N'-Disuccinimidyl carbonate (DSC), 4-Dimethylaminopyridine (DMAP), Dimethylformamide (DMF), rt, 30 min; and then tyramine hydrochloride, N,N-Diisopropylethylamine (DIPEA), room temperature (rt), 2 hours.

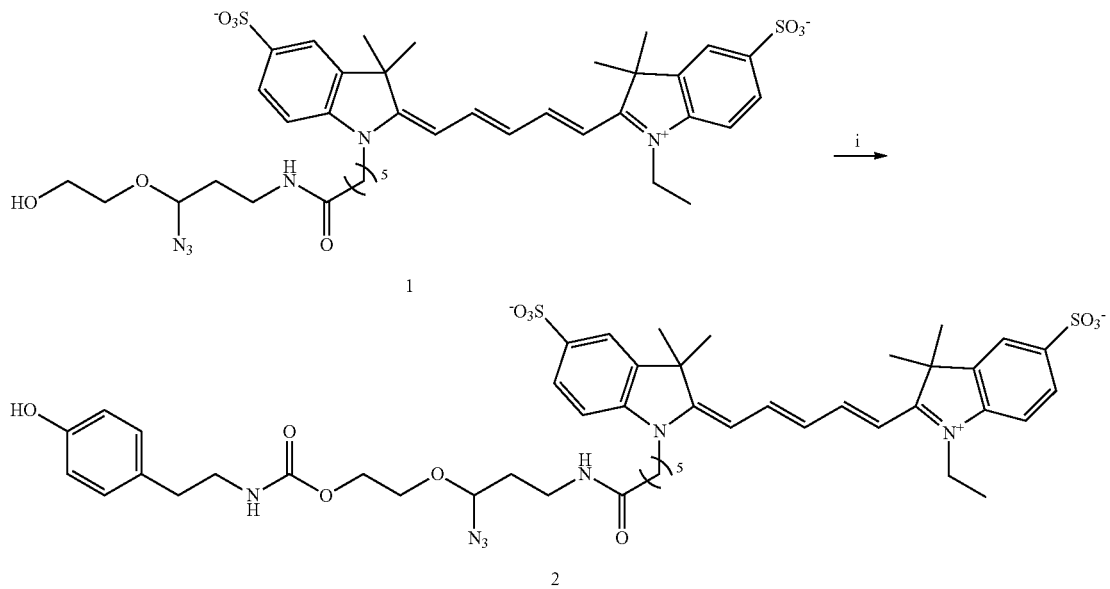

Tyramide-N$_3$-Cy5 (2): The compound 1 prepared accordingly to the literature (Mondal et al., Angew. Chemie Int. Ed. 2017, 56:2636-2639) was further purified by semi-preparative reverse phase HPLC [HPLC gradient: A, 100% 0.1 M TEAA; B, 100% MeCN; 0-2 min, 5% B (flow 2-5 ml/min); 2-15 min, 5-22% B (flow 5 ml/min); 15-20 min, 22-30% B (flow 5 ml/min); 20-30 min, 30-35% B (flow 5 ml/min); 30-32 min, 35-95% B (flow 5 ml/min); 32-35 min, 95% B (flow 5 ml/min); 35-37 min, 95-5% B (flow 5 ml/min); 37-40 min, 5% B (flow 5-2 ml/min)]. The fraction with retention time 25.6 min was collected and dried completely under reduced pressure. The purified compound 1 (3.9 mg, 4.86 μmol) was co-evaporated with anhydrous DMF (1 ml) and then dissolved in anhydrous DMF (300 μL). N, N'-disuccinimidyl carbonate (DSC) (6.2 mg, 24.3 μmol) in 40 μL of anhydrous DMF and 4-dimethylaminopyridine (DMAP) (3.0 mg, 24.3 μmol) were added to the above solution and the reaction mixture was stirred for 30 min at room temperature. Subsequently, to this reaction mixture tyramine hydrochloride (4.2 mg, 24.3 μmol) and N,N-diisopropylethylamine (DIPEA) (8.2 μL, 48.6 μmol) were added and the reaction mixture was stirred for 2 hours at room temperature. After completion of the reaction, DMF was evaporated completely under reduced pressure. The crude product was purified by a preparative silica gel TLC plate (25×25 cm; silica gel 60; CH$_3$OH:CH$_2$Cl$_2$=1:6; Rf=0.2). Subsequently, the residue was dissolved in 0.1 M TEAA buffer/10% CH$_3$CN followed by filtering off undissolved materials by nylon syringe filter (0.2 UM). Then the product was further purified by semi-preparative reverse phase HPLC [HPLC gradient: A, 100% 0.1 M TEAA; B 100% MeCN; 0-2 min, 5% B (flow 2-5 ml/min); 2-10 min, 5-22% B (flow 5 ml/min); 10-15 min, 22-30% B (flow 5 ml/min); 15-20 min, 30-40% B (flow 5 ml/min); 20-25 min, 40-50% B (flow 5 ml/min); 25-30 min, 50-60% B (flow 5 ml/min); 30-32 min, 60-70% B (flow 5 ml/min); 32-35 min, 70-95% B (flow 5 ml/min); 35-37 min, 95% B (flow 5 ml/min); 37-39 min, 95-5% B, (flow 5 ml/min); 39-42 min, 5% B (flow 5-2 ml/min)]. The fraction with retention time 14.1 min was collected and dried completely under reduced pressure. The residue was co-evaporated twice with water (2 ml) to afford compound 2 (1.1 mg, 24%) as a pure blue solid. $^1$H NMR (500 MHz, CD$_3$OD) δ 8.05-7.96 (m, 2H), 7.87-7.77 (m, 4H), 7.29 (dd, J=22.1, 8.4 Hz, 2H), 6.98 (d, J=7.4 Hz, 2H), 6.70 (d, J=8.1 Hz, 2H), 6.55-6.47 (m, 1H), 6.22 (dd, J=24.1, 13.4 Hz, 2H), 4.60 (t, J=5.9 Hz, 1H), 4.16-3.97 (m, 6H), 3.89-3.84 (m, 1H), 3.73-3.64 (m, 2H), 3.21-3.1 (m, 4H), 2.59-2.52 (m, 2H), 2.19-2.12 (m, 2H), 1.83-1.70 (m, 4H), 1.70-1.53 (m, 12H), 1.35-1.22 (m, 6H); HRMS (ESI-, m/z) calcd for $C_{47}H_{58}N_7O_{11}S_2$ [(M)-]: 960.3636, found: 960.3074.

Example 3: Materials and Methods for Examples 1 and 2

Protein Staining with Cleavable Fluorescent Tyramide in Cells

Cell culture: HeLa CCL-2 cells (ATCC) were maintained in Dulbelcco's modified Eagle's Medium (DMEM) supplemented with 10% fetal bovine serum, 100 U/mL penicillin and 100 g/mL streptomycin in a humidified atmosphere at 37° C. with 5% $CO_2$. Cells were plated on chambered coverglass (0.2 ml medium/chamber) (Thermo Fisher Scientific) and allowed to reach 60% confluency in 1-2 days.

Cell fixation: Cultured HeLa CCL-2 cells were fixed with 4% formaldehyde at 37° C. for 15 min, permeabilized with 0.1% (vol/vol) TRITON™ X-100 at room temperature for 15 min, and washed 3 times with 1× phosphate-buffered saline (PBS), each for 5 min.

Endogenous peroxidase blocking: Fixed and permeabilized HeLa CCL-2 cells were incubated with 0.15% $H_2O_2$ in PBT (1×PBS, 0.1% (vol/vol) TRITON™ X-100) for 10 min, and then washed 3 times with 1×PBS, each for 5 min.

Immunofluorescence with cleavable fluorescent tyramide: Fixed and permeabilized HeLa CCL-2 cells were first blocked with 1× blocking buffer (1% (wt/vol) bovine serum albumin, 0.1% (vol/vol) TRITON™ X-100, 10% (vol/vol) normal goat serum) at room temperature for 1 hour. The cells were incubated with HRP-conjugated primary antibodies at a concentration of 5 μg/mL in 1× blocking buffer for 45 min, and then washed 3 times with PBT, each for 5 min. Subsequently, cells were incubated with 10 pmol/μL tyramide-N3-Cy5 in amplification buffer (0.1 M Boric acid, pH=8.5) for 7 min. Cells were quickly washed twice with PBT, followed by 5 min wash with PBT for 3 times. Stained cells were washed with GLOX buffer (0.4% glucose and 10 mM Tris HCl in 2× saline-sodium citrate (SSC) buffer (300 mM sodium chloride, 30 mM trisodium citrate, pH=7.0)) for 1 min at room temperature, and then imaged in GLOX solution (0.37 mg mL-1 glucose oxidase and 1% catalase in GLOX buffer). The following primary antibodies were used: HRP-conjugated rabbit anti-HMGB1 (Thermo Fisher Scientific; PA5-22722), HRP-conjugated rabbit anti-HDAC2 (Abcam; ab195851), HRP conjugated rabbit anti-TDP43 (Abcam; ab193850), HRP-conjugated rabbit anti-PABPN1 (Abcam; ab207515), HRP-conjugated rabbit anti-hnRNP A1 (Abcam; ab198535), HRP conjugated mouse anti-Nucleolin (Abcam; ab198492), HRP-conjugated rabbit anti-Histone H4 (acetyl K16) (Abcam; ab200859), HRP-conjugated mouse anti-hnRNP K (Abcam; ab204456), HRP-conjugated rabbit anti-ILF3 (Abcam; ab206250) and HRP-conjugated mouse anti-Nucleophosmin (Abcam; ab202579).

To stain protein Ki67, fixed and blocked HeLa CCL-2 cells were incubated with 5 μg/mL rabbit anti-Ki67 (Thermo Fisher Scientific; RB1510P1ABX) in 1× blocking buffer for 45 minutes, and then washed 3 times with PBT, each for 5 minutes. Afterwards, cells were incubated with 5 μg/mL HRP-conjugated goat-anti-rabbit (Thermo Fisher Scientific; A16110) in 1% (wt/vol) bovine serum albumin in PBT for 30 minutes, followed by 3 times wash with PBT, each for 5 min. Subsequently, cells were incubated with 10 pmol/μL tyramide-N$_3$-Cy5 in amplification buffer for 7 min. Cells were quickly washed twice with PBT, followed by 5 min wash with PBT for 3 times. Cells were then imaged in GLOX solution.

Fluorophore cleavage and HRP deactivation: To remove the fluorophores and simultaneously deactivate horseradish peroxidase (HRP), cells were incubated with tris(2-carboxyethyl)phosphine (TCEP) (100 mM, pH=9.5) at 50° C. for 30 minutes. To explore the cleavage efficiencies under different temperatures, cells were incubated with TCEP (100 mM, pH=9.5) at 37° C., 50° C., and 65° C. for 30 minutes. To study the cleavage kinetics, cells were incubated with TCEP (100 mM, pH=9.5) at 50° C. for 5, 15, 30, and 60 minutes. Following the TCEP incubation, cells were washed 3 times with PBT and 3 times with 1×PBS, each for 5 min. Cells were then imaged in GLOX solution. To evaluate the HRP deactivation efficiencies following the TCEP incubation, cells were incubated with 10 pmol/μL tyramide-N$_3$-Cy5 in amplification buffer for 7 min. After 2 times quick wash and 3 times 5 min wash with PBT, cells were imaged in GLOX solution.

Conventional immunofluorescence: The Cy5 labeled primary and secondary antibodies were prepared accordingly to the literature. For direct immunofluorescence, fixed and blocked HeLa CCL-2 cells were incubated with 5 μg/mL Cy5 labeled rabbit anti-Ki67 primary antibodies (Thermo Fisher Scientific; RB1510P1ABX) in the 1× blocking buffer for 45 min at room temperature. Cells were washed 3 times with PBT, each for 5 min, and then imaged. For indirect immunofluorescence, fixed and blocked HeLa CCL-2 cells were incubated with 5 μg/mL rabbit anti-Ki67 (Thermo Fisher Scientific; RB1510P1ABX) for 45 min in 1× blocking buffer, then washed 3 times with PBT, each for 5 min. Then cells were incubated with 5 μg/mL Cy5 labeled goat-anti-rabbit (Thermo Fisher Scientific; A16112) in 1% (wt/vol) bovine serum albumin in PBT for 30 min, followed by 3 times wash with PBT, each for 5 min. Cells were then imaged in GLOX solution.

Multiplexed Protein Analysis with Cleavable Fluorescent Tyramide in Cells

Fixed and blocked HeLa CCL-2 cells were incubated with 5 μg/mL HRP conjugated primary antibodies at room temperature for 45 minutes, and then stained by tyramide-N$_3$-Cy5. After imaging, stained cells were incubated with 100 mM TCEP (pH=9.5) at 50° C. for 30 min, followed by the next immunofluorescence cycle. The sequentially used primary antibodies include HRP-conjugated rabbit anti-HMGB1 (Thermo Fisher Scientific; PA5-22722), HRP-conjugated rabbit anti-HDAC2 (Abcam; ab195851), HRP-conjugated rabbit anti-TDP43 (Abcam; ab193850), HRP conjugated rabbit anti-PABPN1 (Abcam; ab207515), HRP-conjugated rabbit anti-hnRNP A1 (Abcam; ab198535), HRP-conjugated mouse anti-Nucleolin (Abcam; ab198492), HRP-conjugated rabbit anti-Histone H4 (acetyl K16) (Abcam; ab200859), HRP-conjugated mouse anti-hnRNP K (Abcam; ab204456), HRP-conjugated rabbit anti-ILF3 (Abcam; ab206250) and HRP-conjugated mouse anti-Nucleophosmin (Abcam; ab202579). For control experiments, fixed and blocked HeLa CCL-2 cells were incubated with 5 µg/mL HRP-conjugated primary antibodies at room temperature for 45 min, and then stained by Cy5 labeled tyramide.

Multiplexed Protein Analysis with Cleavable Fluorescent Tyramide in Brain Tissues Deparaffinization and antigen retrieval: The brain formalin-fixed paraffin-embedded (FFPE) tissue slide was deparaffinized 3 times in xylene, each for 10 min. Then, the slide was immersed in 100% ethanol for 2 min, 95% ethanol for 1 min, 70% ethanol for 1 min, 50% ethanol for 1 min, 30% ethanol for 1 min, and rinsed with deionized water. Subsequently, the slide was immersed in antigen retrieval buffer (10 mM sodium citrate, 0.05% TWEEN™ 20 (2-[2-[3,4-bis(2-hydroxyethoxy)oxolan-2-yl]-2-(2-hydroxyethoxy)ethoxy]ethyl dodecanoate), pH=6.0), and water-bathed in a pressure cooker for 20 min with the "high pressure" setting. Afterwards, the slide was rinsed 3 times with 1×PBS, each for 5 min.

Multiplexed protein staining in FFPE tissues: After deparaffinization and antigen retrieval, the brain FFPE tissue was first blocked by 0.15% $H_2O_2$ for 10 min and then washed 3 times with 1×PBS, each for 5 min. The tissue was then blocked in 1× blocking buffer at room temperature for 1 hour. Subsequently, the tissue was incubated with 5 µg/mL biotin conjugated Rabbit anti-NeuN (Abcam; ab204681) in 1× blocking buffer for 45 min, and then washed 3 times with PBT, each for 5 min. Afterward, the tissue was incubated with 5 µg/mL HRP conjugated streptavidin (Abcam; ab7403) in 1% (wt/vol) bovine serum albumin in PBT for 30 min, followed by 3 times wash with PBT, each for 5 min. Subsequently, the tissue was incubated with 10 pmol/µL tyramide-$N_3$-Cy5 in amplification buffer for 7 min. The tissue was quickly washed twice with PBT, followed by 5 min wash with PBT for 3 times. After imaging, the tissue was incubated with 100 mM TCEP (pH=9.5) at 50° C. for 30 min. The tissue was imaged again to initiate the next cycle. In the following cycles, the tissue was incubated with 5 µg/mL HRP-conjugated primary antibodies in 1× blocking buffer for 45 min. After stained with tyramide-$N_3$-Cy5 and imaged, the tissue was incubated with 100 mM TCEP (pH=9.5) at 50° C. for 30 min and imaged again, followed by the next analysis cycle. The sequentially used primary antibodies include HRP-conjugated rabbit anti-PABPN1 (Abcam; ab207515), HRP-conjugated rabbit anti-HMGB1 (Thermo Fisher Scientific; PA5-22722), HRP-conjugated mouse anti-hnRNP K (Abcam; ab204456), HRP conjugated rabbit anti-TDP43 (Abcam; ab193850), HRP-conjugated rabbit anti-hnRNP A1 (Abcam; ab198535), HRP-conjugated rabbit anti-ILF3 (Abcam; ab206250) and HRP-conjugated mouse anti-Nucleophosmin (Abcam; ab202579).

Imaging and Data Analysis

Both stained cells and the FFPE brain tissue were imaged under a Nikon Ti-E epifluorescence microscope equipped with 20× objective. Images were taken using a CoolSNAP HQ2 camera and Chroma filter 49009. Cell segmentation and intensity quantification were processed by NIS-Elements Imaging software. Pseudo-color images were generated using ImageJ. Protein expression heterogeneity and correlation were analyzed with Excel (Microsoft). The hierarchical clustering with Cluster 3.0. ViSNE maps were generated from CYT.

Example 4: Highly Sensitive and Multiplexed In Situ RNA/DNA Profiling

Fixed frozen tissue sample preparation and pretreatment: Lumbar spinal cord segments were dissected and post-fixed for 2 hours at 4° C. The spinal cords were cryo-sectioned to 14 µm, thaw-mounted onto Superfrost Plus (Fisher Scientific) slides, allowed to dry for 20 minutes at room temperature, and then stored at 80° C.

After post-fixation, cryo-section, and thaw-mounting, spinal cord tissue was successively incubated in 50%, 70%, and 100% ethanol at room temperature for 5 minutes respectively, then baked in the oven at 60° C. for 10 minutes.

Tissue was then incubated with HRP blocking buffer (0.15% $H_2O_2$ in 1×PBT) for 10 minutes at room temperature, and subsequently washed 3 times with 1×PBS at room temperature, each for 5 minutes. A 30 minutes RNAscope® Protease IV (Advanced Cell Diagnostics) treatment at room temperature was performed to the tissue after HRP blocking, followed up with 3 times 1× PBS wash at room temperature, each for 5 minutes.

Multi-channel in situ hybridization: In situ hybridization of the spinal cord tissue was performed using the RNAscope® Multiplex Fluorescent v2 Assay (Advanced Cell Diagnostics). The signal development of each channel was done by staining the slide with 0.25 pmol/µL cleavable Cy5-labeled tyramide (tyramide-$N_3$-Cy5) in amplification buffer (0.0015% $H_2O_2$ and 0.1% TRITON™ X-100 in 0.1 M boric acid, pH=8.5) at 40° C. for 30 minutes. After staining, the slide was washed 3 times with 1× RNAscope® Wash Buffer (Advanced Cell Diagnostics) at room temperature, each for 5 minutes. HRP blocking was subsequently performed by incubating slide with RNAscope® Multiplex FL v2 HRP blocker (Advanced Cell Diagnostics) for 15 minutes at 40° C., followed up with 2 times 1× RNAscope® Wash Buffer wash at room temperature, each for 2 minutes.

After incubation with GLOX buffer (0.4% glucose and 10 mM Tris HCl in 2×SSC) for 1-2 min at room temperature, the stained slide was imaged in GLOX solution (0.37 mg mL$^{-1}$ glucose oxidase and 1% catalase in GLOX buffer).

Fluorescent signal was removed by incubating slide with cleavage solution (100 mM TCEP in 5×SSC, pH=9.5) at 40° C. for 30 min, and 3 times washing with 1× RNAscope® Wash Buffer at room temperature, each for 5 minutes, then followed by the next channel signal development.

Probe stripping: Slide was incubated with 0.5 unit/µL DNase I (Roche Diagnostics) at room temperature for 1 hour, followed up with 6 times wash with DNase quenching buffer (0.3% lithium dodecyl sulfate and 30% formamide in TE buffer) at room temperature, each for 10 minutes.

After DNase treatment, slide was subsequently incubated with 70% formamide in 2×SSC at 40° C. and washed 3 times with 1×PBS at room temperature.

Slide after probe stripping was followed up with next round of multi-channel in situ hybridization.

Imaging: Tissue was imaged under a Nikon Ti-E epifluorescence microscope equipped with a 10× objective. Images were captured using a CoolSNAP HQ2 camera and NIS-Elements Imaging software. Chroma filter 49009 was used for Cy5.

Figure 24:
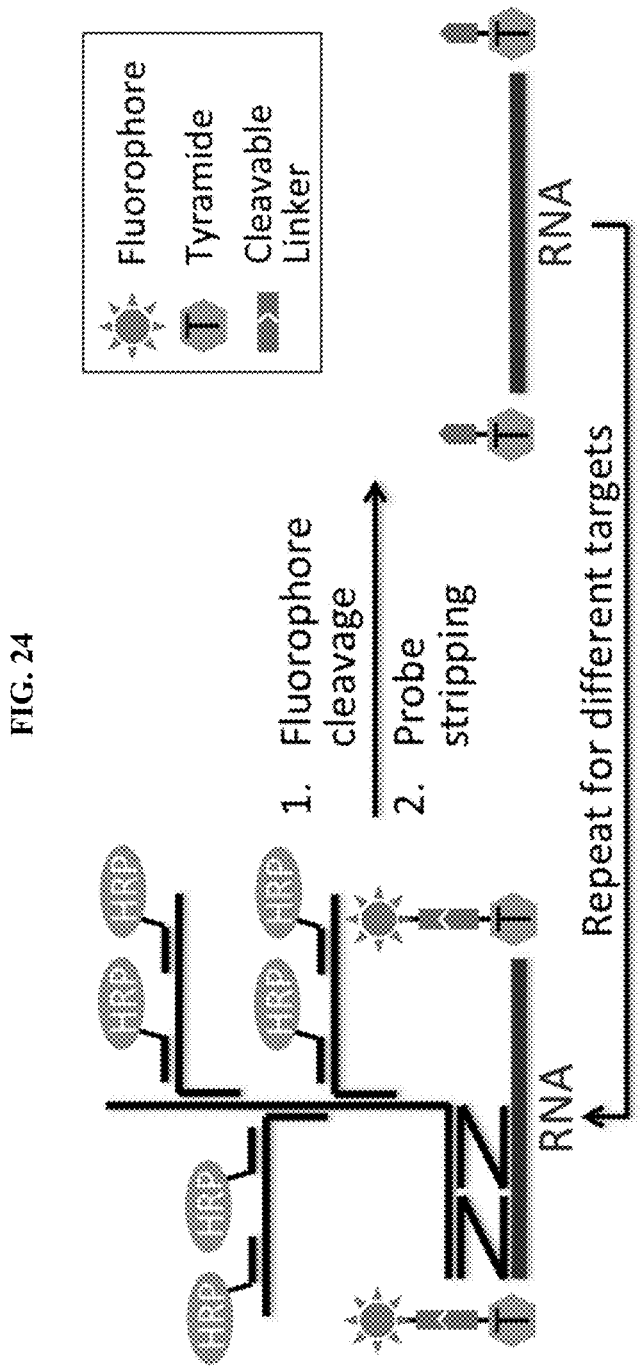
FIG. 24 demonstrates highly sensitive and multiplexed in situ RNA/DNA profiling with cleavable fluorescent tyramide. RNA/DNA targets are stained with HRP-conjugated oligonucleotides and cleavable fluorescent tyramide. After imaging, the fluorophores are chemically cleaved and the oligonucleotide probes are stripped off. Through cycles of target staining, fluorescence imaging, fluorophore cleavage and probe stripping, comprehensive RNA/DNA profiling can be achieved in single cells in situ.
Figure 25:
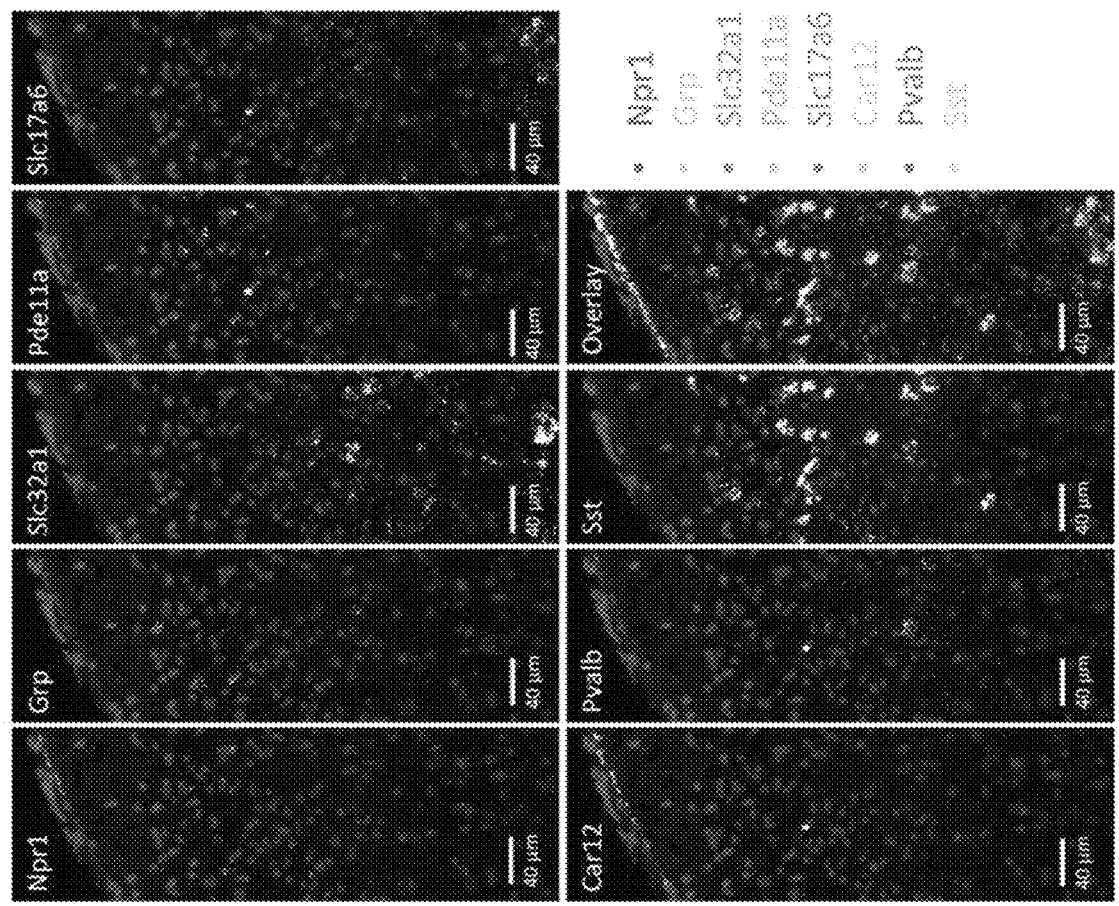
FIG. 25 demonstrates sequential detection of eight different RNAs using HRP-conjugated oligonucleotides and tyramide-N$_3$-Cy5 in mouse spinal cord tissue.

Results: As shown in FIG. 24, staining with HRP-conjugated oligonucleotides and cleavable fluorescent tyramide provides highly sensitive and multiplexed in situ RNA/DNA profiling. After imaging, the fluorophores were chemically cleaved and the oligonucleotide probes were stripped off. FIG. 25 shows sequential detection of eight different RNAs using HRP-conjugated oligonucleotides and tyramide-$N_3$-

Cy5 in mouse spinal cord tissue. These data demonstrate that, through cycles of target staining, fluorescence imaging, fluorophore cleavage and probe stripping, comprehensive RNA/DNA profiling can be achieved in single cells in situ.

Example 5—In Situ Sequential Detection of Proteins and RNAs in Same Tissue

Figure 26:
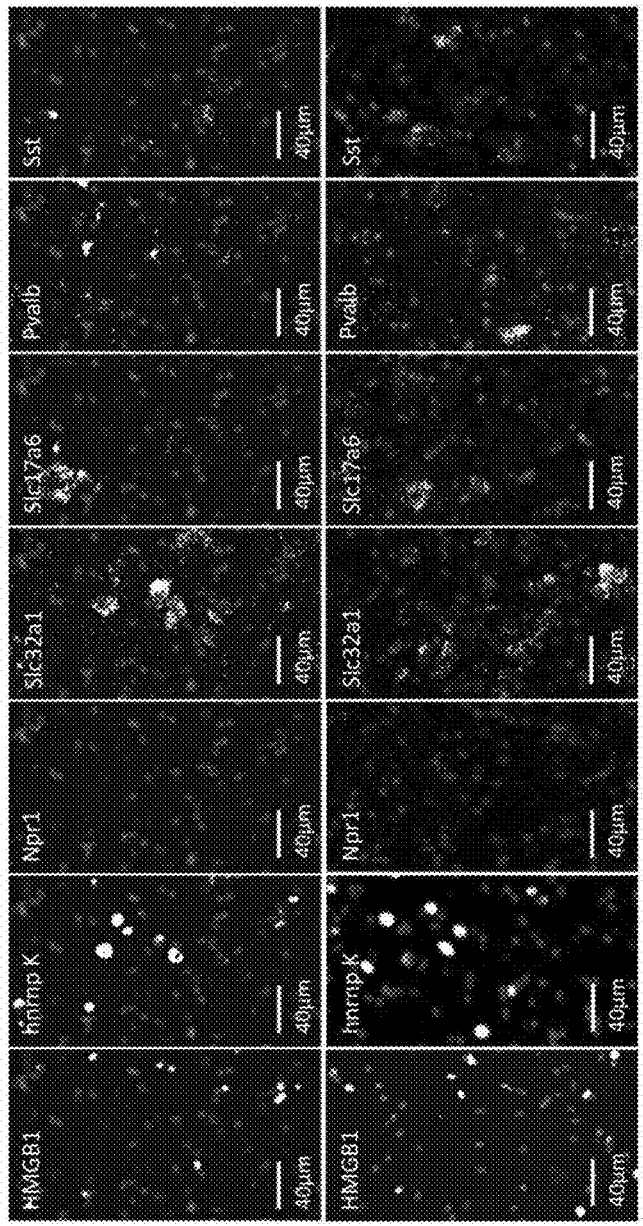
FIG. 26. Top: Two proteins (HMGB1 and hnrnp K) and five different RNAs were detected sequentially with HRP conjugated antibodies and oligonucleotides together with tyramide-N$_3$-Cy5 in the same tissue. Bottom: the same targets are detected in different tissue sections using conventional immunohistochemistry and RNA FISH.

The top images in FIG. 26 demonstrate sequential detection of two proteins (HMGB1 and hnrnp K) and five different RNAs using HRP-conjugated antibodies and oligonucleotides together with tyramide-N3-Cy5 in the same tissue. The bottom images of FIG. 26 demonstrate sequential detection of the same two proteins and five RNAs in different tissue sections using conventional immunohistochemistry and RNA FISH. These data were generated by performing the protein staining protocol of this disclosure for two sequential cycles using HRP conjugated rabbit anti-HMGB1 and HRP conjugated mouse anti-hnRNP K. Next, the RNA staining protocol of this disclosure was performing for the following six cycles.

The present invention has been described in terms of one or more preferred embodiments, and it should be appreciated that many equivalents, alternatives, variations, and modifications, aside from those expressly stated, are possible and within the scope of the invention.

We claim:

1. A method of multiplexed in situ analysis of biomolecules in a tissue, wherein the tissue comprises a plurality of biomolecules, the method comprising the following steps:
   (a) performing a first contacting step comprising contacting the tissue with a plurality of horseradish peroxidase (HRP)-conjugated targeting agents that are configured to specifically bind or hybridize to a target biomolecule in the contacted tissue, wherein the first contacting step occurs under conditions that promote binding or hybridization of the targeting agents to the target biomolecule;
   (b) performing a second contacting step comprising contacting the tissue with a cleavable detectably-labeled tyramide, wherein the second contacting step occurs under conditions that promote conjugation of the cleavable detectably-labeled tyramide to the target biomolecule;
   wherein the cleavable detectably-labeled tyramide consists of, in order, a tyramide, a cleavable linker, and a detectable label;
   (c) imaging the tissue after the second contacting step whereby a detectable signal generated from an interaction of HRP-conjugated targeting agents with the cleavable detectably-labeled tyramide is detected;
   (d) only after the imaging step of (c), cleaving, at the cleavable linker, the detectable label from the detectably-labeled tyramide; and
   (e) optionally consecutively repeating a cycle comprising: the first contacting step, second contacting step, imaging step, and cleaving step,
   wherein the first contacting step of each consecutive cycle utilizes a new plurality of HRP-conjugate targeting agents that bind or hybridize to a different target biomolecule.

2. The method of claim 1, wherein the plurality of biomolecules comprises proteins, RNA, or DNA, or a combination thereof.

3. The method of claim 1, wherein the HRP-conjugated targeting agents are HRP-conjugated antibodies or HRP-conjugated oligonucleotides, or a combination thereof.

4. The method of claim 1, wherein the cleavable detectably-labeled tyramide comprises a fluorophore.

5. The method of claim 4, wherein the fluorophore is selected from the group consisting of Cy5, TAMRA, (13-[2-carboxy-(4 or 5)-(2,5-dioxopyrrolidin-1-yl)oxycarbonylphenyl]-6,7,7,19,19,20-hexamethyl-17-(sulfomethyl)-2-oxa-20-aza-6-azoniapentacyclo[12.8.0.03,12.05,10.016,21]docosa-1 (14),3,5,8,10,12,15,17,21-nonaen-9-yl) methanesulfonate (ALEXA FLUOR™ 594), ATTO 647N, and ATTO 700.

6. The method of claim 1, wherein the cleavable detectably-labeled tyramide is a compound having formula II:

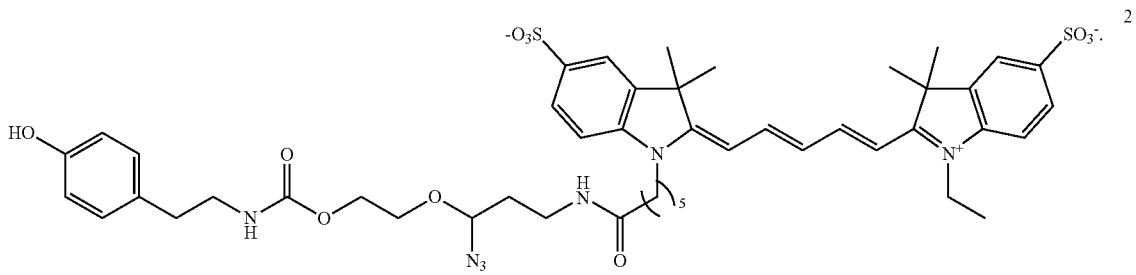

7. The method of claim 1, wherein cleaving the detectable label from the cleavable detectably-labeled tyramide comprises chemically cleaving the detectable label.

8. The method of claim 1, further comprising washing to remove unhybridized targeting agents and non-specifically hybridized targeting agents following the second contacting step.

9. The method of claim 1, wherein the plurality of targeting agents comprises HRP-conjugated synthetic DNA oligonucleotide probes.

10. The method of claim 1, wherein the plurality of targeting agents comprises HRP-conjugated polyclonal antibodies, HRP-conjugated monoclonal antibodies, or HRP-conjugated antigen-binding fragments thereof.

* * * * *